US006822078B2

(12) United States Patent
Ozaki et al.

(10) Patent No.: US 6,822,078 B2
(45) Date of Patent: Nov. 23, 2004

(54) DIAGNOSTIC DRUGS FOR AUTOIMMUNE DISEASES

(75) Inventors: Shoichi Ozaki, Kyoto (JP); Junko Sobajima, Hirakata (JP); Hiroko Uesugi, Kyoto (JP); Takahiro Okazaki, Kyoto (JP); Masao Tanaka, Kyoto (JP); Kazuwa Nakao, Kyoto (JP); Michiteru Yoshida, Nagareyama (JP); Hitoshi Shirakawa, Asaka (JP); Fumio Osakada, Himeji (JP)

(73) Assignee: Kaneka Corp., Osaka (JP)

( * ) Notice: Subject to any disclaimer, the term of this patent is extended or adjusted under 35 U.S.C. 154(b) by 0 days.

(21) Appl. No.: 09/214,881

(22) PCT Filed: May 15, 1997

(86) PCT No.: PCT/JP97/01647

§ 371 (c)(1),
(2), (4) Date: Jun. 7, 1999

(87) PCT Pub. No.: WO98/02744

PCT Pub. Date: Jan. 22, 1998

(65) Prior Publication Data

US 2002/0009749 A1 Jan. 24, 2002

(30) Foreign Application Priority Data

Jul. 17, 1996 (JP) .............................. 8-187945
Oct. 7, 1996 (JP) .............................. 8-266431

(51) Int. Cl.$^7$ .............................. A61K 38/16
(52) U.S. Cl. .................. 530/358; 530/300; 435/975
(58) Field of Search ................. 530/358, 300, 530/350; 435/975, 7.1

(56) References Cited

U.S. PATENT DOCUMENTS 4,281,061 A * 7/1981 Zuk et al.

OTHER PUBLICATIONS

Colman et al. Research in Immunology vol. 145 pp. 33–36, 1994.*

Ayer et al. J. of Rheumatology vol. 21. No. 11 pp. 2071–2075, 1994.*

Clayton et al, "Measurement of antibody to poly (adenosine diphosphate–ribose): its diagnostic value in systemic lupus erythematosus," 1984, pp. 263–271, Clin, exp. Immunol.

Yung, et al, "Sex–Specific Differences in T Cell Homing May Explain Increased Disease Severity in Female Mice," Jul. 1997, pp. 1334–1343, vol. 40 No. 7, Arthritis & Rheumatism.

Neuer et al., "Autoantibodies to the Chromosomal Protein HMG–17 in Juvenile Rheumatoid Arthritis," Apr. 1992, pp. 472–475, vol. 35 No. 4, Arthritis & Rheumatism.

"Anti–Neutrophil cytoplasmic antibodies (ANCA) in ulcerative colitis; anti–cathepsin G and a novel antibody correlate with a refractory type;" J. Sobajima, S. Ozaki, T. Okazaki, F. Osakada, S. Sumita, K. Mori & K. Nakao; 1996 Blackwell Science Ltd, Clinical and Experimental Immunology; pp. 120–124.

"Antineutrophil cytoplasmic autoantibodies, autoantigens, and systemic vasculitis;" Wolfgang L. Gross, Elena Csernok and Udo Helmchen; 1995 APMIS 103, pp. 81–97.

Bettina Witteman, et. al., "Autoantibodies to Nonhistone Chromosomal Proteins HMG–1 and HMG–2 in Sera of Patients with Juvenile Rheumatoid Arthritis," Arthritis and Rheumatism, vol. 33, No. 9, P1378–1383, (1990).

International Search Report dated Oct. 14, 1997.

Ayer, L.M. et al., Arthritis & Rheumatism, *Antibodies to HMG Proteins in Patients with Drug–Induced Autoimmunity*, vol. 37, No. 1, Jan. 1994, pp 98–103.

Adachi, Yoshifumi et al., Journal of Chromatography, *Efficient Large–Scale Purification of Non–Histone Chromosomal Proteins HMG1 and HMG2 by using Polybuffer–Exchanger PBE94*, 530 1990, pp. 39–46.

Yoshida, Michiteru et al., Journal of Biochemistry, *Unwinding of DNA by Nonhistone Chromosomal Protein HMG(1+2) from Pig Thymus as Determined with Endonuclease*, 95, 1984, pp. 117–124.

* cited by examiner

Primary Examiner—Patrick J. Nolan
Assistant Examiner—Eaon Smallwood
(74) Attorney, Agent, or Firm—Howrey Simon Arnold & White LLP

(57) ABSTRACT

A diagnostic drug and a diagnostic kit for autoimmune diseases including at least one of a polypeptide selected from an HMG-1 family, a polypeptide selected from an HMG-2 family, a fragment thereof which is reactable with an antibody of an autoimmune disease patient, and a method for detecting an antibody of an autoimmune disease patient using the same are provided.

5 Claims, 15 Drawing Sheets

Elution conditions   Column: YMC-ProteinRP, 250X4.6mmID, 5μm

Flow rate: 1.5ml/min.

Elution: A:0.1%TFA, B: 80%CH₃CN/0.1%TFA

30%B→45%B/30min

Detection: 214nm

1 Neutrophil lysate
2 Purified 28kDa antigen
3 Purified 29kDa antigen

1 Neutrophil lysate
2 Primary antibody absorbed with bovine HMG-1 and HMG-2 in the experiment of lane 1.
3 HMG-1 and HMG-2 purified from HL-60
4 Primary antibody absorbed with bovine HMG-1 and HMG-2 in the experiment of lane 3.

(HMG−1+HMG−2) μg/ml

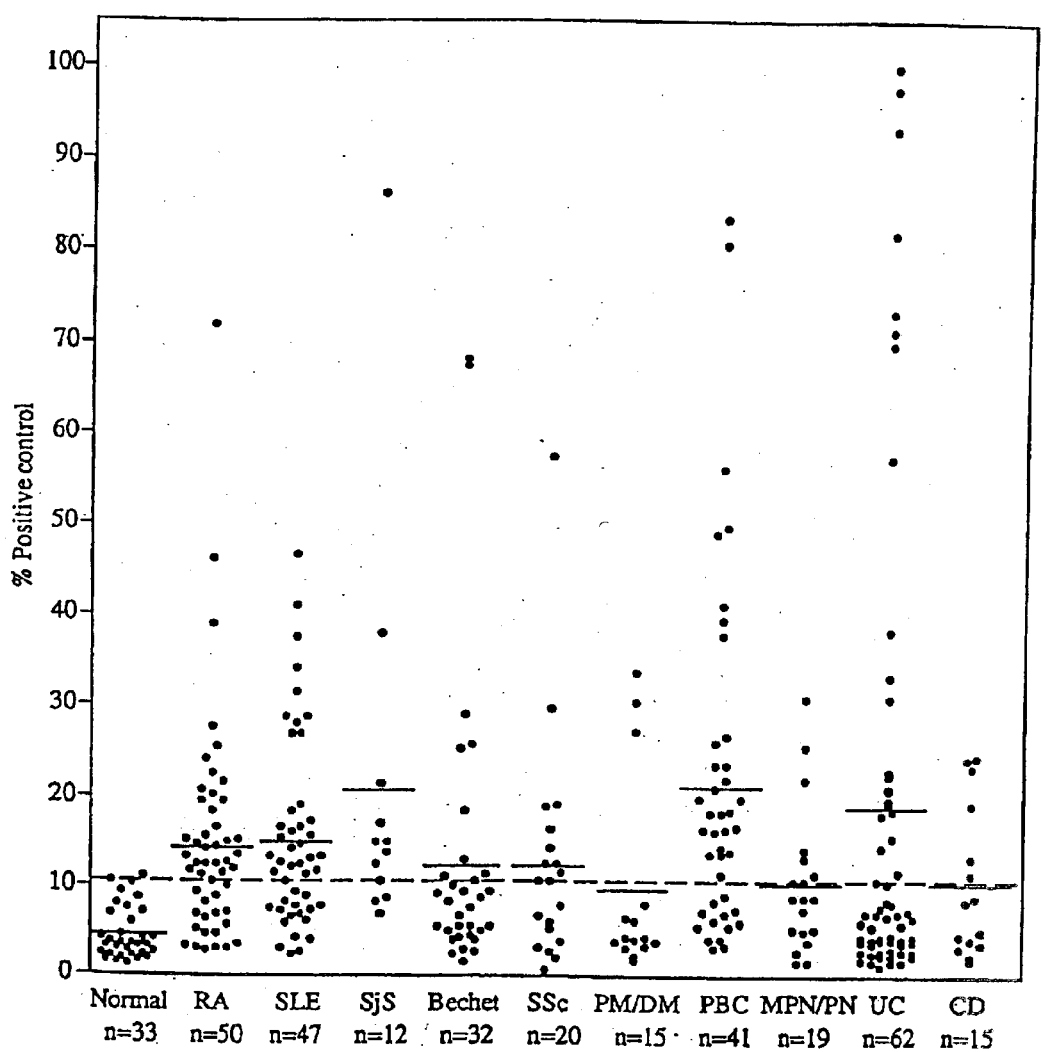

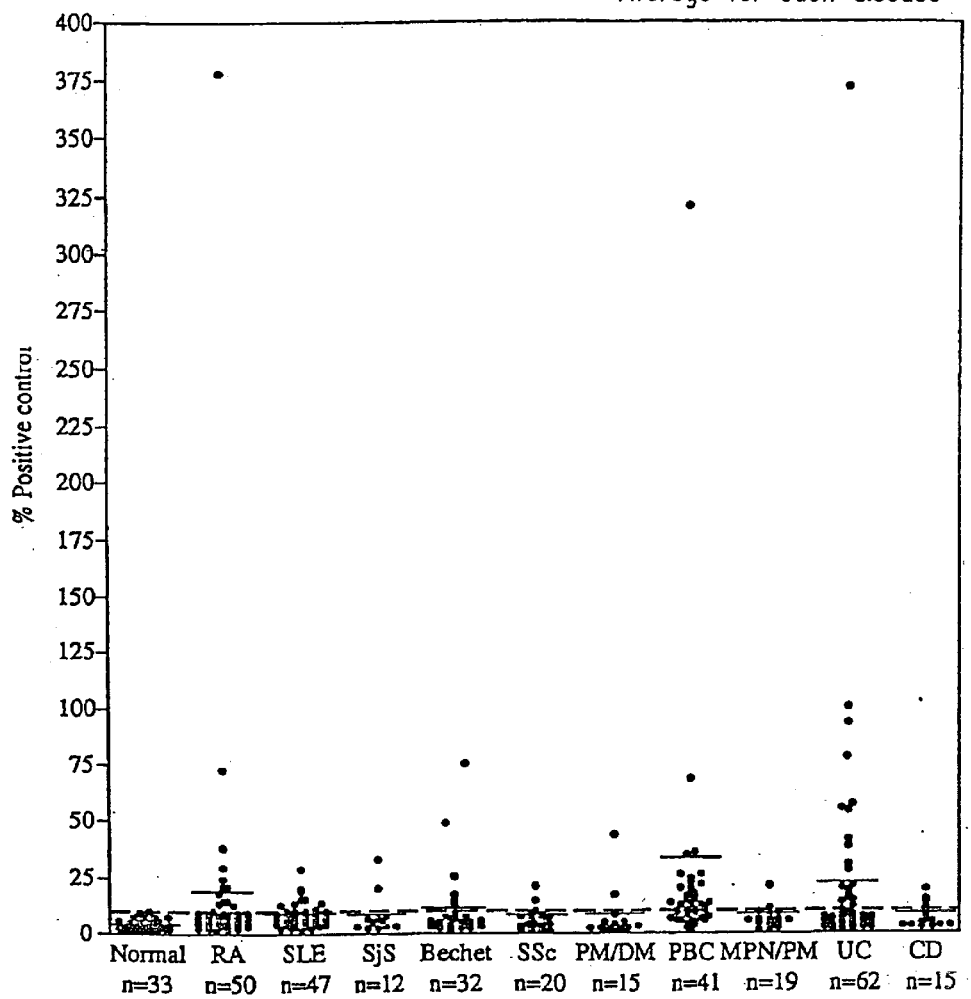

FIG. 15

```
Human    1 GKGDPKKPRGKMSSYAFFVQTCREEHKKKHPDASVNFSEFSKKCSERWKT 50
           |||||||||||||||||||||||||||||||||||||||||||||||||
Porcine  1 GKGDPKKPRGKMSSYAFFVQTCREEHKKKHPDASVNFSEFSKKCSERWKT 50
           |||||||||||||||||||||||||||||||||||||||||||||||||
Bovine   1 GKGDPKKPRGKMSSYAFFVQTCREEHKKKHPDASVNFSEFSKKCSERWKT 50
           |||||||||||||||||||||||||||||||||||||||||||||||||
Rat      1 GKGDPKKPRGKMSSYAFFVQTCREEHKKKHPDASVNFSEFSKKCSERWKT 50

Human   51 MSAKEKGKFEDMAKADKARYEREMKTYIPPKGETKKKFKDPNAPKRPPSA 100
           |||||||||||||||||||||||||||||||||||||||||||||||||
Porcine 51 MSAKEKGKFEDMAKADKARYEREMKTYIPPKGETKKKFKDPNAPKRPPSA 100
           |||||||||||||||||||||||||||||||||||||||||||||||||
Bovine  51 MSAKEKGKFEDMAKADKARYEREMKTYIPPKGETKKKFKDPNAPKRPPSA 100
           |||||||||||||||||||||||||||||||||||||||||||||||||
Rat     51 MSAKEKGKFEDMAKADKARYEREMKTYIPPKGETKKKFKDPNAPKRPPSA 100

Human  101 FFLFCSEYRPKIKGEHPGLSIGDVAKKLGEMWNNTAADDKQPYEKKAAKL 150
           |||||||||||||||||||||||||||||||||| |||||||||||||
Porcine101 FFLFCSEYRPKIKGEHPGLSIGDVAKKLGEMWNNTAADDKHPYEKKAAKL 150
           |||||||||||||||||||||||||||||||||||||||||||||||||
Bovine 101 FFLFCSEYRPKIKGEHPGLSIGDVAKKLGEMWNNTAADDKQPYEKKAAKL 150
           |||||||||||||||||||||||||||||||||||||||||||||||||
Rat    101 FFLFCSEYRPKIKGEHPGLSIGDVAKKLGEMWNNTAADDKQPYEKKAAKL 150

Human  151 KEKYEKDIAAYRAKGKPDAAKKGVVKAEKSKKKKEEEEDEEDEEDEEEEE 200
           |||||||||||||||||||||||||||||||||||||||||||||||||
Porcine151 KEKYEKDIAAYRAKGKPDAAKKGVVKAEKSKKKKEEEEDEEDEEDEEEEE 200
           |||||||||||||||||||||||||||||||||||||||||||||||||
Bovine 151 KEKYEKDIAAYRAKGKPDAAKKGVVKAEKSKKKKEEEEDEEDEEDEEEEE 200
           |||||||||||||||||||||||||| ||||||||||||||||||||||
Rat    151 KEKYEKDIAAYRAKGKPDAAKKGVVKAEKSKKKKEEEEDDEEDEEDEEEEE 200

Human  201 DEEDEDEEEDDDDE 214
           |||||  ||||||||
Porcine201 DEEDEEEEDDDDE 214
           |||||  ||||||||
Bovine 201 DEEDEEEEDDDDE 214
           ||||||||||||||
Rat    201 EEEDEDEEEDDDDE 214
```

Comparison among human, porcine, bovine and rat HMG-1
"|" indicates the same amino acid with that of human HMG-1.

FIG. 16

```
Human    1  GKGDPNKPRGKMSSYAFFVQTCREEHKKKHPDSSVNFAEFSKKCSERWKT  50
            |||||||||||||||||||||||||||||||||||| |||||||||||||
Porcine  1  GKGDPNKPRGKMSSYAFFVQTCREEHKKKHPDSSVNFAEFSKKCSERWKT  50
            ||||||||||||||||||||| |||||||||| ||||    |||||
Bovine   1  GKGDPNKPRGKMSSYAFFVQTSREEHKKKHPDASVNF----S----ERWKT 50
            |||||||||||||||||||||| |||||||||||||||||||||||||||
Rat      1  GKGDPNKPRGKMSSYAFFVQTCREEHKKKHPDSSVNFAEFSKKCSERWKT  50

Human   51  MSAKEKSKFEDMAKSDKARYDREMKNYVPPKGDKKGKKKDPNAPKRPPSA 100
            ||||||||||||||||||||||||||||||||||||||||||||||||||
Porcine 51  MSAKEKSKFEDMAKSDKARYDREMKNYVPPKGDKKGKKKDPNAPKRPPSA 100
            ||||||||||||||||||||||||||||||||||||||||||||||||||
Bovine  51  MSAKEKSKFEDMAKSDKARYDREMKNYVPPKGDKKGKKKDPNAPKRPPSA 100
            |||||||||||| |||||||||||||||||||||||||||||||||||||
Rat     51  MSAKEKSKFEDLAKSDKARYDREMKNYVPPKGDKKGKKKDPNAPKRPPSA 100

Human  101  FFLFCSEHRPKIKSEHPGLSIGDTAKKLGEMWSEQSAKDKQPYEQKAAKL 150
            ||||||||||||||||||||||||||||||||||||||||||||||||||
Porcine 101 FFLFCSEHRPKIKSEHPGLSIGDTAKKLGEMWSEQSAKDKQPYEQKAAKL 150
            ||||  |||||||| |||||||||||||||||||||||||||||| |||
Bovine  101 FFLFSAEHRPKIKAEHPGLSIGDTAKKLGEMWSQQSAKDKQPYEQKASKL 150
            ||||||||||||||||||||||||||||||||||||||||||||||||||
Rat     101 FFLFCSEHRPKIKSEHPGLSIGDTAKKLGEMWSEQSAKDKQPYEQKAAKL 150

Human  151  KEKYEKDIAAYRAKGKSEAGKKGPGRPTGSKKKNEPEDEEEEEEEE-DED 199
            |||||||||||||| ||||||||||||||||||||||||||||||| |||
Porcine 151 KEKYEKDIAAYRAKGKGEAGKKGPGRPTGSKKKNEPEDEEEEEEEEEDED 200
            ||||| |||||||||||||||||||||||||||||||||||||||
Bovine  151 KEKYEKX-AAYRAKGKSEAGKKGPGRPTGSKKKNEPEDEEEEEE...... 200
            ||||||||||||||| ||||||||||||||||||||||||||||| |||
Rat     151 KEKYEKDIAAYRAKGKSEVGKKGPGRPTGSKKKNEPEDEEEEEEEEDDED 200

Human   200 EEEEDEDEE 208
            |||||||||
Porcine 201 EEEEDEDEE 209

Bovine  201 ..........
            |||||||||
Rat     201 EEEEDEDEE 209
```

Comparison among human, porcine, bovine and rat HMG-2
"|" indicates the same amino acid with that of human HMG-2.

DIAGNOSTIC DRUGS FOR AUTOIMMUNE DISEASES

This application is a 35 USC 371 aplication of PCT/JP97/0164 filed on May 5, 1997.

TECHNICAL FIELD

The present invention relates to a diagnostic drug for and a kit for diagnosing autoimmune diseases, and a method for detecting an antibody of an autoimmune disease patient using high mobility group protein-1 (HMG-1), high mobility group protein-2 (HMG-2), or a fragment of a polypeptide thereof with which the antibody of the autoimmune disease patient reacts. In particular, the present invention relates to a diagnostic drug for and a kit for diagnosing rheumatoid arthritis, systemic lupus erythematosus, Sjögren's syndrome, Behçet's disease, scleroderma, primary biliary cirrhosis, microscopic polyangiitis/polyarteritis nodosa, ulcerative colitis, Crohn's disease, and autoimmune hepatitis, and a method for detecting an antibody of a patient of any of the above-mentioned diseases, using HMG-1, HMG-2, or a fragment of a polypeptide thereof with which the antibody of such a patient reacts.

BACKGROUND ART

It has been reported that various anti-neutrophil cytoplasmic antibodies (ANCA) are involved in autoimmune and inflammatory diseases. ANCA are antibodies capable of being detected by indirect immunofluorescence assay (IIF) and are classified into cytoplasmic-ANCA (cANCA) and perinuclear-ANCA (pANCA). cANCA is detected in Wegener's granulomatosis patients at a frequency of as high as 80%, and the antigen to cANCA is proteinase-3 (PR-3) in 90% or more of all the cases. pANCA is detected in microscopic polyangitis, and pauci-immune necrotizing crescentic glomerulonephritis (NCGN) patients at a frequency of as high as 80%, and the antigen to the antibody is myeloperoxidase (MPO-ANCA) in 80% of all the cases. Early-phase diagnosis and differential diagnosis of angiitis syndromes are realized by measurement of highly disease-specific antibodies.

Recently, pANCA has been found in the patients suffering from inflammatory diseases including inflammatory bowel disease (IBD) such as ulcerative colitis (UC), rheumatoid arthritis (RA), systemic lupus erythematosus (SLE), autoimmune hepatitis (AIH), malignant tumors, amebic abscesses, and sweet disease. As antigens to pANCA, lactoferrin, cathepsin G, elastase, lysozyme and the like have been identified. Causes of these diseases and relationship of these antigens and the diseases have been studied. The specificity of these antigens to pANCA is low, which suggests that there are other antigens involved.

Generally, the ratios at which ANCA is detected in the patients (percentages of positive patients) of ulcerative colitis (UC) and Crohn's disease (CD), which are both inflammatory bowel diseases, by the indirect immunofluorescence assay are 40 to 87% and 6 to 27%, respectively. Judging by the staining pattern, pANCA is detected at a high percentage of 80 to 95% in the case of ulcerative colitis, whereas pANCA and cANCA are equivalently detected in the case of Crohn's disease. pANCA is detected at a high percentage in the case of rheumatoid arthritis, systemic lupus erythematosus and Sjögren's syndrome, and the percentages are 33% (4%), 43% (2%) and 50% (8%), respectively. The numerals in parentheses are percentage of cANCA-positive patients.

As antigens to ANCA detected in ulcerative colitis and Crohn's disease, various antigens have been reported including lactoferrin, cathepsin G, myeloperoxidase, and myeloperoxidase+elastase, and myeloperoxidase+elastase+cathepsin G. However, antigens specific to these diseases have not been identified so far. Antigens of other diseases involving pANCA have not been identified, either.

Standard diagnostic methods for ulcerative colitis and Crohn's disease include endoscopy, biopsy, and X-ray examination. These methods are costly, painful, and time-consuming. Recently, detection of pANCA by indirect immunofluorescence assay has been reported as a serodiagnosis for ulcerative colitis. However, this method is not sufficiently sensitive and tends to have an increased background signal. Serodiagnosis, by which neutrophils and other cells are fixed on a plate with ethanol, has a further disadvantage in that the result depends on the state of the cells and the fixing technique and is not sufficiently reliable. Accordingly, serodiagnosis has not been in general use. Regarding Crohn's disease, even an autoantibody has not been found. As described above, a specific and simple diagnostic method for autoimmune diseases has not been developed.

In rheumatoid arthritis and systemic lupus erythematosus, various autoantibodies such as a rheumatoid factor and antinuclear antibody are produced. In scleroderma, polymyositis, Behçet's disease, and periarteritis nodosa, few autoantibodies are detected and thus clinical symptoms are main factors for diagnosis. It has been pointed out that early diagnosis of these diseases is important to prevent progress of the disease in prognostic phase by sufficient therapy. However, a simple serodiagnostic method has not been developed.

In general, when a patient is suspected to have an autoimmune disease, examination of an antinuclear antibody is used for diagnosis at primary screening. Antinuclear antibody is a general term for autoantibodies, the antigens to which are cell nucleic acids and various nucleic protein components, and includes various antibodies. Antinuclear antibodies are mainly detected by the indirect immunofluorescence assay. As the antinuclear antibodies, anti-DNA antibody, anti-histone antibody, anti-ENA antibody, anti-centromere antibody, and anti-nuclear antibody are assumed which are classified by the staining pattern. However, it has been pointed out that there are many problems in uniformalizing the measurement precision of antinuclear antibodies. The problems include, for example, that the nucleus materials (cells) vary in accordance with the research facilities, the calibration curve cannot be obtained, and the autoantibodies are non-uniform. The most serious problem is that the method relies on visual observation and thus the determination criterion and technology are not objective.

Despite these problems, measurement of antinuclear antibodies by indirect immunofluorescence assay is now indispensable to diagnosis of various collagen diseases including systemic lupus erythematosus and understanding of clinical conditions thereat. Needless to say, it is demanded to identify autoantigens of autoimmune diseases other than the antinuclear antibody and to develop a simple and objective method for detecting antibodies using the antigens, with no difference among research facilities.

As can be appreciated, it leads to establishment of diagnosis of an autoimmune disease and appropriate therapeutic strategies to identify an autoantigen of an autoimmune disease patient and to detect an autoantibody using the autoantigen. It is demanded to identify and isolate a common autoantigen in autoimmune diseases and to develop a simple method for detecting an antibody using the antigen.

DISCLOSURE OF INVENTION

As a result of active studies in order to overcome the above-described problems with the prior art, the present inventors succeeded for the first time in history in isolating high mobility group protein-1 (HMG-1) and high mobility group protein-2 (HMG-2), which are known proteins, using antibodies in the sera of the autoimmune disease patients, especially pANCA-positive ulcerative colitis patients. HMG-1 and HMG-2 were isolated and identified as novel antigens with which the antibodies react (Sobajima J. et al., Clin. Exp. Immunol. 105:120–124, 1996; Sobajima J. et al., Clin. Exp. Immunol. 107:135–140, 1997). By constructing an ELISA system using the HMG-1 and HMG-2, the present inventors showed that a high percentage of antibodies of the patients of rheumatoid arthritis, systemic lupus erythematosus, Sjögren's syndrome, Behçet's disease, scleroderma, primary biliary cirrhosis, microscopic polyanglitis/polyarteritis nodosa, ulcerative colitis, Crohn's disease and autoimmune hepatitis are positive to these antigens. By showing that the ELISA system is more sensitive, simpler, more reliable and more objective than measurement for antinuclear antibodies by indirect immunofluorescence assay, the present inventors found that antibodies against the antigens can be markers for diagnosis of rheumatoid arthritis, systemic lupus erythematosus, Sjögren's syndrome, Behçet's disease, scleroderma, primary biliary cirrhosis, microscopic polyangiitis/polyarteritis nodosa, ulcerative colitis, Crohn's disease and autoimmune hepatitis. Thus, the present invention has been completed.

The HMG antigens were previously measured as one of antinuclear antibodies of autoimmune diseases, not as an antigen to ANCA. Dennis J. S. et al. reported at the systemic lupus erythematosus patients have an anti-HMG-1 antibody at a radio of 10. % and an anti-HMG-2 antibody at a ratio of 6.9%, and that the mixed connective-tissue disease patients and the rheumatoid arthritis patients have both antibodies at a ratio of 0% (Science 215, 1245–1247, 1982). Briolay J. et al. detected an anti-HMG-1 antibody and an anti-HMG -2 antibody by immunoblotting assay from the patients of systemic lupus erythematosus, rheumatoid arthritis and scleroderma, and reported that neither antibody has a diagnostic value (Autoimmunity, 2, 165–176, 1989). It is assumed they had problems in the purity of the HMG antigens, the techniques such as the ELISA assay and the immunoblotting assay, the state of e patients and the number of the subjects, but an invention relating to a diagnostic drug using 11MG-1 and HMG-2 had not been completed at the time of the above-mentioned publications. There is a report that 39% of the antinuclear antibody-positive juvenile rheumatism patients are positive with respect to the anti-HMG-1 antibody and/or anti-HMG-2 antibody (Wittemann B. et at., Arthritis and Rheumatism 33, 1378–1383, 1990). The present inventors constructed as ELISA system using highly pure HMG-1 and HMG-2 and measured the percentage of the patients who were positive to these antigens regarding various diseases. As a result, a significant difference from the healthy (or normal) persons was found in ten diseases. Thus, the present invention has been completed.

The present invention relates to a diagnostic drug for autoimmune diseases, comprising at least one of a polypeptide selected from an HMG-1 family, a polypeptide selected from an HMG-2 family, a fragment thereof which is reactable with an antibody of an autoimmune disease patient, a kit for diagnosing these diseases, and a method for detecting an antibody of an autoimmune disease patient.

When the polypeptide is a neutrophil 28 kDa antigen (HMG-2), the autoimmune disease is not ulcerative colitis.

In a preferred embodiment of the invention, the autoimmune disease is rheumatoid arthritis, systemic lupus erythematosus, Sjögren's syndrome, Behçet's disease, scleroderma, primary biliary cirrhosis, microscopic polyangiitis/polyarteritis nodosa, ulcerative colitis, Crohn's disease, or autoimmune hepatitis.

In a preferred embodiment of the invention, the polypeptide is selected from human, bovine, porcine, chicken, mouse or rat HMG-1 or HMG-2.

Thus, the objectives of the present invention are achieved.

BRIEF DESCRIPTION OF DRAWINGS

FIG. 13 shows scatter diagram in accordance with disease obtained using porcine HMG-1 as an antigen;

FIG. 14 is a scatter diagram in accordance with disease obtained using HMG-2 as an antigen;

FIG. 15 compares amino acid sequences of human, porcine, bovine and rat HMG-1; and FIG. 16 compares amino acid sequences of human, porcine, bovine and rat HMG-2.

BEST MODE FOR CARRYING OUT THE INVENTION

Figure 1:
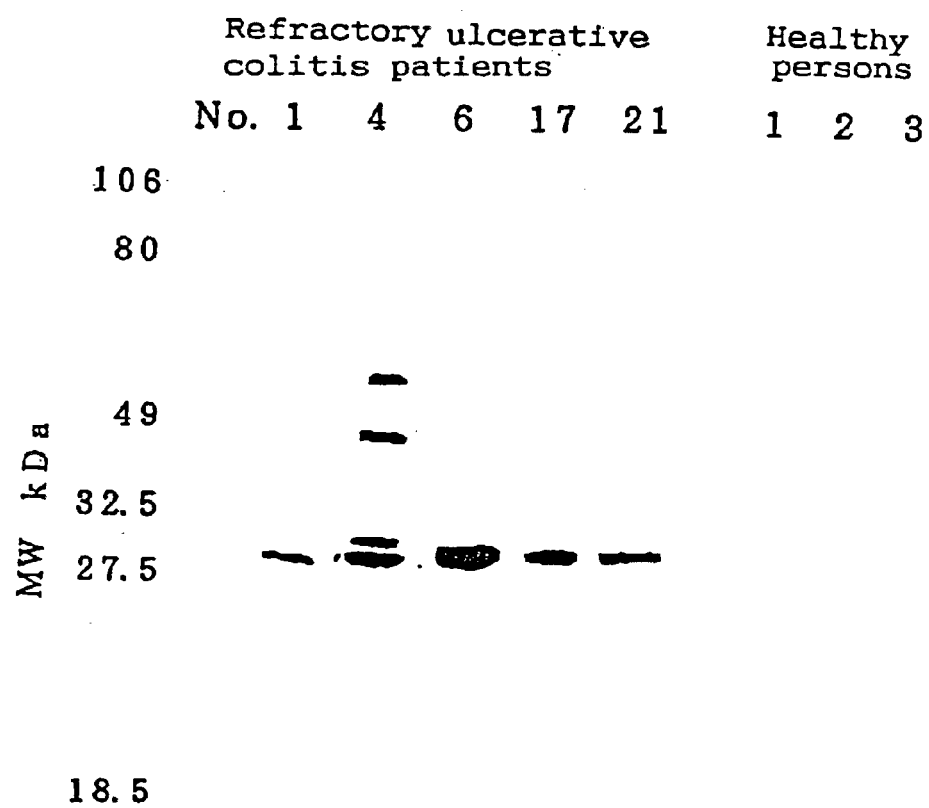
FIG. 1 shows the results of Western blotting performed on neutrophil cytoplasm lysate (antigen), separated from the peripheral blood of healthy persons after electrophoresis on SDS-PAGE using purified IgG (antibody) obtained from the serum of five ulcerative colitis patients and three healthy persons.

HMG (high mobility group protein) was found in 1964 as a non-histone protein contained in a large quantity in a chromatin structure, and is ubiquitously contained in all the higher animals and plants. HMG has been found to exist in the cytoplasm in abundance as well as in the nucleus. HMG has not been clearly known in terms of physiological functions but is considered to act as any of a wide range of transcription promoting factors and nucleosome relax factors which change the structure of DNA into an optimum structure during transcription reaction to promote the transcription activity for the following reasons. HMG is bonded to DNA. Although bonding to DNA, HMG is not specif to any particular nucleotide sequence and relaxes the double helix structure. There are several types of HMG.

The polypeptide used for the present invention is a polypeptide selected from the HMG-1 family or HMG-2 family or a fragment thereof.

The HMG-1 (high mobility group protein-1) family refers to polypeptides having an amino acid homology of 90% or more with human HMG-1 indicated by SEQ NO: 1 and includes, for example, bovine HMG-1 (SEQ NO: 3), porcine HMG-1 (SEQ NO: 4), and rat HMG-1 (SEQ NO: 5). Human HMG-1 is preferable, but porcine, bovine and rat HMG-1 are usable due to the high homology. FIG. 15 compares the amino acid sequences of these types of HMG-1.

The HMG-2 (high mobility group protein-2) family refers to polypeptides having an amino acid homology of 80% or more with human HMG-2 indicated by SEQ NO: 2 and includes, for example, porcine HMG-2 (SEQ NO: 6), partial sequence of bovine HMG-2 (SEQ NO: 7), rat HMG-2 (SEQ NO: 8), chicken HMG-2 (SEQ NO: 9), chicken HMG-2a (SEQ NO: 10), and mouse HMG-2 (SEQ NO: 11). Human, porcine and bovine HMG-2 are preferable. FIG. 16 compares the amino acid sequences of these types of HMG-2.

The polypeptides belonging to the HMG-1 or HMG-2 family include a polypeptide having deletion, substitution or addition of one or more amino acid, or a fragment thereof which can react with an antibody from autoimmune disease patients.

The fragment refers to a fragment which can react with an antibody from autoimmune disease patients among the fragments of polypeptides belonging to the HMG-1 or HMG-2 family. The fragment can be chemically synthesized or prepared using an appropriate proteolytic enzyme. Whether the prepared fragment reacts with an antibody or not can be determined by reacting the fragment with serum obtained from autoimmune disease patients. This method is well known among those skilled in the art, and the same technique as used for antibody detection described below can be used.

HMG-1 and HMG-2 are proteins ubiquitously contained in all the cells and thus can be prepared by extraction from any organ, tissue, or cell. HMG-1 and HMG-2 are extracted from, for example, human thymus, porcine thymus, bovine thymus, human placenta, neutrophil, and HL-60 cell line. Extraction and purification methods are known and are described in, for example, M. Yoshida and K. Shimura, J. Biochem, Tokyo, 95, 117–124, 1980) and Y. Adachi et al., J. Chromatogr., 530, 39–46, 1992). A mixture of bovine HMG-1 and bovine HMG-2 is commercially available from Wako Pure Chemical.

A polypeptide belonging to the HMG-1 or HMG-2 family is produced from the above-mentioned tissues or culture cells producing the polypeptide, or by introducing a vector incorporating a gene encoding the polypeptide into a host cell and expressing the polypeptide. A polypeptide having deletion, substitution or addition of one or more amino acid can be produced by a well-known method based on, for example, a HMG-1 or HMG-2 gene sequence; for example, by modifying the gene sequence through site-directed mutagenesis or deletion mutagenesis using M13 phage and expressing the polypeptide. The host cell can be a prokaryote or eukaryote; e.g., bacteria such as *Escherichia coli* and *Bacillus*, yeast, mold, insect cell, and mammal cell. Polypeptide can be purified by a well-known method, for example, chromatography such as gel filtration chromatography, ion exchange chromatography, affinity chromatography, or reverse phase liquid chromatography performed independently or in combination. Preferably, reverse phase HPLC or ion exchange chromatography are usable. A column for reverse phase HPLC can be any of various commercially available columns, but a protein separation column, for example, YMC-protein RP column (YMC) is preferably usable. Usable for ion exchanger chromatography are, for example, polybuffer-exchanger PBE94 column or Mono Q column (Pharmacia).

The autoimmune diseases to which the present invention relates include rheumatoid arthritis, systemic lupus erythematosus, Sjögren's syndrome, Behçt's disease, scleroderma, polymiositis/dermatomyositis, primary biliary cirrhosis, microscopic polyangiitis/polyarteritis nodosa, ulcerative colitis, Crohn's disease, and autoimmune hepatitis.

Ulcerative colitis in the present invention has the following symptoms. Ulcerative colitis refers to an idiopathic, nonspecific inflammatory disease of large intestine, especially rectum, which mainly attacks mucosa and submucous layer. This disease often attacks adults of 30 years old or younger, but is also found in children and adults of 50 years old or older. The cause is not known and is considered to be related to immunological mechanisms, or genetic or psychological factors. Usually, diarrhea with hematochezia and various systemic symptoms are shown. When it lasts long and attacks the entire large intestine, it tends to be malignant. Refractory ulcerative colitis refers to cases in which the ulcerative colitis is under precise medical therapy and still (1) shows chronic persistence, (2) is active for six months or longer after recrudescence or (3) repeats recrudescence frequently.

Crohn's disease is a cryptogenic inflammatory intestine disease which can possibly attack all the digestive organs including small and large intestines. This disease is characterized by non-continuity, segmen lesion, longitudinal ulcer, full-thickness inflammatory lesion (tumor or stegnosis) or non-tyrogenous granuloma. It often attacks young people (15 to 24 years old). The autoantibody has not been found, and there is no simple serodiagnostic method.

Rheumatoid arthritis (RA) is a cryptogenic refractory chronically progressive disease. The essence of RA is a chronic synovitis which does not show any tendency of autotherapy. Invasion of lymphocyte, vascularization, and stratification and proliferation of synovial membrane cell are observed. Small joints of arms and legs and large joints of knee, elbow, shoulder and coxa are attacked symmetrically. Persistence of synovitis and proliferation of inflammatory tissues at these joints destroy cartilage and bone at a later stage, resulting in joint deformation or physical handicap.

Systemic lupus erythematosus is a multi-organ disease and accompanies various diseases. Non-infectious inflammatory lesion occurs in almost all the tissues and organs in the entire body including cutaneous symptoms such as butterfly, oral cavityulcer, arthritis, lupusnephritis, and supraneural lesion. Various autoantibodies are produced, but an autoantibody specific to the disease has not been specified. Expression ratio of antinuclear antibody by indirect immunofluorescence assay is almost 100% for diagnosis, but the specificity is not high. It significantly often attacks young women. The survival ratio recently exceeds 95%, but the symptoms last long. Remission and exacerbation are often repeated.

Sjögren's syndrome is a chronic inflammatory disease of exocrine gland, mainly lacrimal gland and salivary gland or water secretion tissues. It is a sicca syndrome of the oral cavity and eye due to reduction in the amount of lacrimation and sialorrhea. It involves only a sicca syndrome in most cases, but sometimes accompanies thyroid gland, lung, stomach and intestines, liver and kidney disorders. In about 30 to 40% of the cases, rheumatoid arthritis, systemic lupus erythematosus and scleroderma are accompanied. It sometimes shows clinically varied symptoms. Sthenia of erythrocyte sedimentation rate, hypergammaglobulinemia and various autoantibodies are recognized. By immunological examination, various autoantibodies are found by immunological examination, and rheumatoid factor (80%) and antinuclear antibody are found in more than half of the cases.

Scleroderma (systemic sclerosis) is a connective-tissue disease accompanying sclerosis of skin and organ disorders. It includes various types and is not necessary systemic or progressive. It accompanies sclerosis of skin in a large part of the entire body (generalized scleroderma) and organ disorders of esophagus, intestines, lung, liver and thyroid gland or the like. There are various types including a highly progressive type having unfavorable prognosis and a type referred to as CREST syndrome having favorable prognosis. In the case of the CREST syndrome, the skin sclerosis is limited to face, hands and fingers and the viscus lesion appears gradually. Among the antinuclear antibodies, anti-Sc1-70 antibody, which is an antibody to topoisomerase-1, is highly specific to a. generalized type of scleroderma (percentage of positive patients: 30%). An anti-centromere antibody has a high diagnostic value to the CREST syndrome. An anti-Ku antibody has a high diagnostic value to duplicated syndrome of scleroderma and polymyositis.

Primary biliary cirrhosis often attacks middle-age or older women and is a chronic disease (symptomatic) characterized by sweet itch and icterus. There is also a silent case which is accidentally found without any symptoms. It starts with destruction of interlobular ductules, and gradually increases fibrous tissue. Then, it leads to tissue image of cirrhosis. These changes in and around ductules is reflected in the clinical image characterized by persistent icterus. The cause is not known. Primary biliary cirrhosis is known to accompany autoimmune diseases (e.g., Sjögren's syndrome and rheumatoid arthritis) in about 30% of the cases, whether silent or symptomatic.

Polymyositis (PM) is a disease by which non-purulent inflammation is systematically caused to skeletal muscle, thus causing myalgia and reduction in myodynamia. A type of PM which accompanies reddish purple helioptope on the eyelid or Gottron symptom of the back of the hand and finger joints is referred to as dermatomyositis (DM). This disease first attacks proximal muscle among striated muscle, as a result of which the patient is unable to stand up or raise the arm. In a serious case, the patient is unable to support the neck and head. In some cases, cancer or malignant tumor are accompanied, in which case cancer therapy must be done first.

Behçet's disease is a cryptogenic refractory disease showing, as main clinical symptoms, recurrent aphthous ulcer of intraoral mucosa (expression ratio: 99%); skin symptoms (84%) such as erythema nodosum, acne-like rash, and subcutaneous thrombophlebitis; stimulated sthenia of skin such as sensitivity to shaving and reaction to needles; and eye symptoms (90%) such as iridocyclitis and chrioretinopathy. It also shows, as side symptoms, arthritis and digestive organ symptoms.

Polyarteritis nodosa is a representative necrotizing angiitis causing systematic inflammatory in arteries. This disease is rare and is difficult to diagnose, but requires therapy at early stage. Arteritis shows various lesions systemically, and skin lesion, kidney lesion, digestive organ lesion, central nervous system lesion and the like are especially important for diagnosis. This disease often attacks men and no antinuclear antibody is found.

Autoimmune hepatitis (hereinafter, referred to as "AIH") is a representative autoimmune hepatitis as well as primary biliary cirrhosis (PBC). Whereas PBC involves autoimmune response to epitheliocyte of ductules, AIH is considered to involve autoimmune response to liver cell components. It often attacks women, and is clinically characterized by expression of various autoantibodies including hyperglobulinemia and antinuclear antibody and accompaniment of fevescence, articular pain, and autoimmune diseases including collagen diseases. Among the autoantibodies, antinuclear antibody (ANA) capable of reacting with intranuclear components (about 70 to 90%) and anti-smooth muscle antibody (66%) capable of reacting with smooth muscle are most often found. The antinuclear antibody is not necessarily specific to AIH and is also found in other autoimmune diseases, specifically systemic lupus erythematosus (SLE). The anti-smooth muscle antibody, unlike the antinuclear antibody, has a low percentage of positive patients in the case of autoimmune diseases such as SLE, and is relatively specific to AIH.

An antibody is a component which exists in a bodily fluid of an autoimmune disease patient and is induced by a specific antigenic substance. For example, an antibody of an ulcerative colitis patient or an antibody of a rheumatoid arthritis patient respectively refers to a component contained in the bodily fluid such as serum of a patient diagnosed to have ulcerative colitis or rheumatoid arthritis. Antibodies of autoimmune diseases include, for example, IgM, IgG, IgE, IgD and IgA.

A diagnostic drug according to the present invention includes a polypeptide contained in the HMG-1 or HMG-2 family or a fragment thereof. The diagnostic drug includes at least one type of polypeptide contained in the HMG-1 or HMG-2 family or a fragment thereof. A mixture of HMG-1 and HMG-2 is preferably used.

A diagnostic drug according to the present invention reacts with an antibody of an autoimmune disease patient to form an antigen/antibody complex. Accordingly, the drug can include a further component for detecting the resultant antigen/antibody complex. Such a component is suitable to methods such as, for example, precipitation reaction method, ELISA assay, RIA, and Western blotting.

The polypeptide contained in the HMG-1 or HMG-2 family or a fragment thereof is used in a diagnostic kit. The diagnostic kit can include, for example, an ELISA plate having a polypeptide contained in the HMG-1 or HMG-2 family or a fragment thereof immobilized thereon and a reagent for detecting an antigen/antibody complex bonded to an antibody of an autoimmune disease patient. The reagent includes a component suitable to methods such as precipitation reaction, ELISA, RIA, and Western blotting. As a detecting reagent, a secondary antibody reagent is, for example, used for an ELISA assay. The secondary antibody reagent is goat or mouse anti-human IgG or anti-human (IgA+IgG+IgM) and reacts with human IgG, IgM and IgA. The secondary antibody reagent can be generally tagged with a tagging agent used in immune measurement methods. Usable tagging agents include, for example, radioisotope (e.g., $^{32}$P, $^{3}$H, $^{125}$I), enzyme (e.g., β-galactosidase, peroxidase, alkali phosphotase, glucoseoxidase, lactate oxidase, alcoholoxidase, mono-amineoxidase), coenzyme and prosthetic group (e.g., FAD, FMN, ATP, biotin, heme), fluoroscein derivatives (e.g., fluoroscein isothiocyanate, fluoroscein thioflubamyl), rhodamine derivatives (e.g., tetramethyl rhodamine B isothiocyanate), Umbelliferone and 1-anilino-8-naphthalenesulfonic acid, and luminol derivatives (e.g., luminol, isoluminol). Alkali phosphotase and peroxidase are preferably used. A preferable substrate for the former is paranitrophenyl phosphoric acid, and a preferable substrate for the latter is tetramethyl benzidine (TMBZ). The antibody and tagging agent can be bonded by a method appropriately selected from known methods as described in text books (for example, "Zoku Seikagaku Jikken Koza 5 Men'eki Seikagaku Kenkyuho" (Lecture on Biochemical Experiments, second series, 5, Immune Biochemistry Study Method), pp. 102–112, 1986, K. K. Tokyo Kagaku Dojin). Many tagged secondary antibodies are commercially available. For example, alkali phosphotase-tagged goat anti-human IgG F(ab')$_2$ polyclonal antibody is available from Immunotech S.A. (France).

The kit can be of a format in which the antigen is accommodated in an appropriate carrier in the format of container, resin, membrane or film, or the antigen is fixed on an appropriate carrier in the format of container, resin, membrane or film.

The carrier can be formed of synthesized organic polymeric compounds such as, for example, polyvinyl chloride, polystyrene, styrene-divinylbenzene copolymer, styrene-anhydride maleic acid copolymer, nylon, polyvinyl alcohol, polyacrylamide, polyacrylonitrile, polypropylene, and polymethylene methacrylate; polysaccharides such as, for example, dextran derivatives (e.g., Sephadex), agarose gel (e.g., Sepharose, Biogel) and cellulose (e.g., paper desk, filter); and inorganic high molecular weight compounds such as glass, silica gel and silicone. These materials can contain a functional group such as amino group, carboxyl group, carbonyl group, hydroxyl group, or sulfhydryl group introduced thereto. Preferable materials include polystyrene and polyvinyl chloride.

The carrier can be of any form, for example, flat plate (e.g., microtiter plate, disk) particles (e.g., beads), tube (e.g., test tube), fiber, membrane, microparticles (e.g., latex particles), capsules, or endoplasmic reticulum-like substance. A preferable form can be selected in accordance with the measurement method. Preferably, a 96-well microtiter plate, with which a large quantity of subjects can be treated in an ELISA system, is used. For example, EB plate (Labosystems), H-type plate and C-type plate (Sumitomo Bakelite), Maxisorp plate (Nunc), and E.I.A./R.I.A. plate (Costar) can be used.

The carrier and the antigen are bonded to each other by a known method such as, for example, physisorption, ionic bond, covalent bond, or entrapping (see, for example, Ichiro Chibata, ed., "Koteika Koso" (Immobilized Enzyme), Mar. 20, 1975, Kodansha). Physisorption is especially preferable due to the simplicity. The antigen and the carrier can be bonded to each other directly or through another substance (e.g., spacer) interposed therebetween. The immobilized antigen can be blocked by a blocker such as gelatin or BSA to restrict non-specific bonding.

A method for detecting an antibody of an autoimmune disease according to the present invention includes the step of reacting a polypeptide selected from the HMG-1 family, a polypeptide selected from the HMG-2 family, or a fragment thereof (antigen) with a bodily fluid component of an autoimmune disease patient. The reaction conditions can be well known conditions in the art. A method-for detecting a substance obtained by the antigen/antibody reaction can also be a known method in the art. Usable detection methods include, for example, precipitation reaction, ELISA, RIA and Western blotting. Detection is performed as follows, for example. Serum from the patient appropriately diluted and the antigen are reacted with each other and washed. Next, an alkali phosphotase-tagged anti-human IgG antibody is added and reacted. Then, p-nitrophenyl phosphoric acid, which is a substrate of alkali phosphotase, is added and colored. The absorbance at 405 nm is measured. Thus, measurement for an anti-HMG-1 antibody and an anti-HMG-2 antibody can be performed.

The kit according to the present invention can include, in addition to the HMG antigen, an appropriate reagent, selected in accordance with the measurement method, from a coloring reagent, a reaction-terminating reagent, a standard antigen reagent, a sample pre-processing reagent and the like.

Hereinafter, using an ulcerative colitis patient as an example, a method of screening an antigen capable of reacting with an antibody of the patient and specifying that the antigen is HMG-1 and HMG-2, and a method for performing measurement for an anti-HMG-1 antibody and an anti-HMG-2 antibody by an ELISA system using the HMG-1 and HMG-2 antigens will be described.

First, blood is sampled from an ulcerative colitis patient to obtain a serum component. Next, the serum component is measured for anti-neutrophil cytoplasmic antibody (ANCA) by indirect immunofluorescence assay. From peripheral blood of healthy persons, a neutrophil fraction is separated by specific gravity centrifugation. Next, the neutrophil fraction is treated to obtain neutrophil lysate and Western blotting is performed. For example, $10^6$ neutrophils are dissolved in a sample buffer containing 2-mercaptoethanol and SDS and boiled for 10 minutes. After the resultant substance is rapidly cooled with ice, SDS-polyacrylamide gel electrophoresis (SDS-PAGE) is performed. After electrophoresis, the protein band is transferred to a nylon membrane and non-specific bonding is blocked using skim milk or the like.

Serum from an ANCA-positive patient is applied to protein A column to purify an IgG antibody fraction. The purified IgG antibody fraction and the neutrophil lysate transferred to the nylon membrane are reacted to each other.

After the nylon membrane is washed, chemical light emission is caused by, for example, a detecting agent such as ECL kit (Amersham), thereby detecting the band. Thus, the antigen is determined to exist.

According to the above-described method, antigenic polypeptide can be confirmed to exist. Such an antigenic polypeptide can be purified by any known protein purification method.

Alternatively, a cell line producing an antigenic polypeptide can be specified using the above-described antibody. An antigenic polypeptide can be produced using such a cell line and purified by any known protein purification method.

By the above-described method, the antigen of 28 kDa to the anti-neutrophil cytoplasmic antibody (ANCA) could be specified. As described in an example below, at least one antigen of 28/39.5/44/47/58 kDa was detected in ten out of 24 ANCA-positive patients. Among the ten patients, seven had 28 kDa antigen. Five out of the seven patients had been diagnosed to have refractory ulcerative colitis. No positive band was detected in the ulcerative colitis patients who were found to be ANCA-negative by indirect immunofluorescence assay. The molecular weight of the antigen according to the present invention is determined by 10% SDS-PAGE.

As a result of screening cells producing a 28 kDa antigen by the above-described screening method, HL-60 cell line (ATCC CCL-240), which is a neutrophil-type cell derived from premyelogenetic leukemia, was found to have a 28 kDa antigen. The results of Western blotting suggested that the HL-60 cell line includes 29 kDa antigen as well as 28 kDa antigen. From the HL-60 cell line, the 28 kDa and 29 kDa antigens can be purified. The 28 kDa and 29 kDa antigens can be purified by any known protein purification method. For example, HL-60 cell line is cultured in a RPMI1640 medium containing 5% FCS added thereto, and the cells are dissolved in 6M guanidine hydrochloride and treated with sonication to inactivate the proteolytic enzymes. The protein is completely dissolved and concentrated by dialyses, for example, ultrafiltration, and simultaneously the solution is substituted with PBS. From the resultant aqueous solution, a 28 kDa antigen and a 29 kDa antigen can be purified. Preferably, reverse phase HPLC is usable. By performing fractionation with reverse phase HPLC using acetonitrile concentration gradient, a 28 kDa antigen and a 29 kDa antigen having a purity of 90% or more can be purified. The conditions for reverse phase HPLC using acetonitrile concentration gradient can be well known conditions.

As a result of analyzing the amino acid sequence of the purified proteins, the 29 kDa was identified as high mobility group protein-1 (HMG-1) and the 28 kDa was identified as high mobility group protein-2 (HMG-2).

After the purified IgG from the antibody-positive patient was absorbed with bovine HMG-1 and HMG-2, reaction with the purified 28 kDa antigen and with the purified 29 kDa antigen was checked with Western blotting. The reaction did not occur. From these results, the antigens were confirmed to be HMG-1 and HMG-2.

HMG-1 and HMG-2 fractions were prepared from human thymus and porcine thymus and Western blotting was performed. These fractions were found to react with the antibody from the patient.

The amino acid sequence of human HMG-1 is different from the porcine, bovine and rat HMG-1 (FIG. 13) only by two, one, and two amino acids, respectively. Accordingly, HMG-1 of these animals can be used for ELISA in lieu of human HMG-1. The amino acid sequence of human HMG-2 is different from the porcine and rat HMG-2 (FIG. 14) only by two amino acids. Accordingly, the porcine HMG-2 can be used in lieu of human HMG-2. Regarding the bovine HMG-2, only a partial sequence is determined and the reported sequence is not considered to be accurate (the bovine sequence is reprinted from the protein databank PIR B61611). HMG-1 and HMG-2 are considered to conserve the amino acid sequence therebetween quite satisfactorily. Considering the high analogy between human and porcine HMG-2, bovine HMG-2 is not considered to be different from human HMG-2 by more than two amino acids. This is also suggested by the result of the above-described absorption experiment that the antibody of the patient was absorbed with bovine HMG-1 and HMG-2 and did not react with human HMG-1 or HMG-2.

HMG-1 and HMG-2 can be simply prepared from human, porcine or bovine thymus tissue in accordance with the method described in the above-mentioned publication. An exemplary method for preparing HMG-1 and HMG-2 from human thymus tissue will be briefly described. Thymus tissue of a child is cut into thin strips and suspended in 0.075M NaCl/0.025M EDTA (pH7.5). Then, the cells are destroyed by a polytron homogenizer. Chromatin is recovered by centrifugation and suspended in 0.35M NaCl (pH7). Then, HMG attached to chromatin is freed by homogenization. Impurities are removed by centrifugation, and trichloro acetic acid is added to the resultant supernatant so as to obtain a 2% trichloro acetic acid solution. The solution is left at 4° C. for for 2 hours, thereby precipitating insoluble proteins other than HMG-1 and HMG-2. The supernatant is recovered by centrifugation and precipitated with ammonia/acetone. The precipitated HMG-1 and HMG-2 are recovered by centrifugation. The precipitates are washed with 90% acetone and dried. This fraction is dissolved in 6M guanidine hydrochloride, and substitution and concentration to PBS by dialysis is performed. Thus, HMG-1 and HMG-2 fractions are obtained. There sultant HMG-1 and HMG-2fractions react with an antibody of an ulcerative colitis patient by Western blotting.

The porcine HMG-1 and porcine HMG-2 used in the present invention were specimens having a purity of 95% or more prepared and purified by the method of Yoshida et al. (Y. Yoshida and K. Shimura, J. Biochem., Tokyo, 95, 117–124, 1980 and Y. Adachi et al., J. Chromatogr., 530, 39–46, 1992). Y. Yoshida is one of the present inventors. These porcine HMG-1 and HMG-2 reacted with the antibody of the patient, like human HMG-1 and HMG-2.

Commercially available bovine HMG-1 and HMG-2 (Wako Pure Chemical) reacted with an antibody of an ulcerative colitis patient. Accordingly, HMG-1 and HMG-2 are considered to be antigens of ulcerative colitis.

An ELISA system was constructed with purified porcine HMG-1 and HMG-2 in accordance with the above-described method. 50 $\mu$l of 5 $\mu$g/ml porcine HMG-1 or HMG-2 is added to each well of a 96-well ELISA plate (Nunc) and left in a stationary state at 4° C. for 24 to 36 hours. After the excess antigen is removed, blocking is performed with 5% BSA. Serum from a patient appropriately diluted with 5% BSA is added and left in a stationary state at room temperature for 2 hours. After each well is washed with a washing liquid, alkali phosphotase-tagged goat anti-human IgG F(ab')$_2$ is added and reacted at room temperature for 2 hours. After each well is washed 5 times with a washing liquid, a paranitrophenyl phosphoric acid (Sigma) solution (10% diethanolamine solution) is added and reacted at room temperature for 20 to 25 minutes. Then, absorbance at 405 nm is measured.

Using this system, standard curves were calibrated using serum of an ulcerative colitis patient who was positive to both an anti-HMG-1 antibody and an anti-HMG-2 antibody. Regarding both antigens, concentration-dependent curves were obtained. These results show that measurement for an anti-HMG-1 antibody and an anti-HMG-2 antibody can be performed regarding various diseases using this ELISA system.

Patients of various autoimmune diseases, i.e., rheumatoid arthritis, systemic lupus erythematosus, Sjögren's syndrome, Behçet's disease, scleroderma, polymyositis/dermatomyositis, primary biliary cirrhosis, microscopic polyangiitis/polyarteritis nodosa, ulcerative colitis, Crohn's disease, autoimmune hepatitis (AIH), hepatitis C and hepatitis B, and healthy persons were measured for an anti-HMG-1 antibody and an anti-HMG-2 antibody. As a result, HMG-1 had a higher antigenicity and more patients were anti-HMG-1 antibody positive compared to HMG-2 among the patients of seven diseases other than primary biliary cirrhosis, ulcerative colitis, Behçet's disease, AIH, hepatitis B and hepatitis C. Regarding HMG-1, the patients of 11 diseases other than polymyositis/dermatomyositis and hepatitis B, a statistically significant difference from the healthy persons was shown. As a result of comparison with a percentage of antinuclear antibody-positive patients obtained by indirect immunofluorescence assay, the percentage of the anti-HMG antibody-positive patients were equal to or higher than the percentage of the antinuclear antibody-positive patients among eight out of the 13 diseases. This indicates the possibility that measurement of an anti-HMG-1 antibody and an anti-HMG-2 antibody can be a diagnostic method for autoimmune diseases replacing detection of an antinuclear antibody by indirect immunofluorescence assay. When used with the detection of antinuclear antibody, the measurement of an anti-HMG-1 antibody and an anti-HMG-2 antibody can diagnose a wider range of autoimmune diseases more accurately.

HMG-1 and HMG-2 are identified as antigens to pANCA. HMG-1 and HMG-2 were previously identified as intranuclear proteins and can possibly be antigens to antibody which has conventionally been referred to as an antinuclear antibody. Accordingly an anti-HMG-1 antibody and an anti-HMG-2 antibody can be detected in antinuclear antibody-positive diseases as well as in the pANCA-positive diseases. Since the ELISA assay is more sensitive than indirect immunofluorescence assay, it is possible to detect an anti-HMG-1 antibody and an anti-HMG-2 antibody in the diseases which have been considered to be ANCA-negative or to have a low ANCA-positive percentage. These diseases include, for example, Wegener's granulomatosis, leukoocyte destructive angiitis, Churs-Strauss syndrome, primary biliary cirrhosis, mixed connective-tissue disease, malignant tumor, amebic abscess, sweet disease, multiple sclerosis, Alzheimer's disease, Hashimoto's disease, hyperthyrea, erythroleukemia.

Neutrophils have high kinetic ability and active phagocytosis. Neutrophils are one of the cells which are the first to travel to the inflammatory location when an inflammatory occurs in the living body. Neutrophils destroy and fuse inflammatory tissues and finally remove and absorb damaged tissues. In many cases of tissue damages in autoimmune diseases, neutrophils invade a local site and are considered to assist inflammation. When inflammation lasts long or remission and exacerbation of inflammation are repeated, neutrophils frequently invade and form pus corpuscles by phagocytosis. It is considered that this exposes the protein in the neutrophils to T cells or B cells and thus antibodies are produced. Assuming that antibodies produced in this manner are anti-HMG-1 and anti-HMG-2 antibodies (mainly, anti-HMG-1 antibody), these antibodies are possibly produced from the initial stage of crisis of autoimmune diseases. Thus, it is possible to diagnose autoimmune diseases at early stage by measurement for an anti-HMG-1 antibody and an anti-HMG-2 antibody.

During the active period of inflammation, production of the HMG antigens possibly occurs in the activated cells in the inflammatory locations as well as in the neutrophils. It is considered that production of anti-HMG antibodies is increased by the MG antigens freed by the destruction of the cells. Accordingly, measurement for an anti-HMG-1 antibody and an anti-HMG-2 antibody can possibly be an index of activity of the disease.

The present invention is also directed to a kit for performing measurement for an anti-HMG-1 antibody and an anti-HMG-2 antibody using ELISA. According to another method, the specificity to the disease can be detected by checking the response between peripheral blood lymphocyte and HMG-1 and HMG-2 of an autoimmune disease or an inflammatory disease patient. The disease can be detected by measuring whether or not T lymphocyte proliferates in response to HMG-1, HMG-2 or a synthetic peptide thereof which is immuno-responsive, or by measuring whether or not y-interferon is produced by macrophage in the same assay.

When HMG is freed by destruction of neutrophil in the inflammatory location, measurement for HMG itself can possibly be an index of activity of the disease. The measurement for HMG can be performed by sandwich ELISA or immunoprecipitation. According to sandwich ELISA, for example, a monoclonal anti-HMG antibody is immobilized on a plate and bonded to purified HMG. Then, the resultant substance is reacted with serum from a patient, and the bonded anti-HMG antibody is detected by anti-Ig antibody tagged with HRP or the like. In the case of immunoprecipitation, HMG and serum from a patient are reacted to each other in a solution and then reacted with an anti-Ig antibody tagged with $I^{125}$ or the like. The radioactivity of the precipitated substance obtained by antigen/antibody reaction is counted. Thus, measurement for HMG can be performed.

EXAMPLES

Hereinafter, the present invention will be described by way of illustrative examples with reference to the accompanying drawings.

Example 1

Detection of Anti-neutrophil Cytoplasmic Antibody (ANCA) by the Indirect Immunofluorescence Assay Peripheral blood was sampled from 35 ulcerative colitis patients (16 males and 19 females) and centrifuged (4° C., 13 minutes, 2000 rpm), thereby obtaining serum components. The percentage of the positive components with respect to the anti-neutrophil cytoplasmic antibody (ANCA) was measured by the indirect immunofluorescence assay. As a control, blood sampled from 10 Crohn's disease patients (9 males and 1 female) was treated in a similar manner and subjected to the same measurement.

The measurement conditions for the indirect immunofluorescence assay using ethanol-fixed human neutrophils will be described below.

First, peripheral blood is treated with specific gravity centrifugation using the Ficoll-Hypaque technique to separate the neutrophils, and the neutrophils are applied to slides at the ratio of $10^5$ neutrophils/slide by cytospin. Then, the slides are dried by cool air from a dryer and washed with PBS (0.8% NaCl/0.02% KCl/10 mM $Na_2HPO_4$/1.5 mM $KH_2PO_4$ pH7.4). Sample sera are each diluted at 1:10 with PBS, and 20 $\mu$l of the resultant sample is put on the slides and reacted at room temperature for 1 hour in a humidified chamber. After the reaction is completed, the resultant substance is washed with PBS. FITC-tagged rabbit anti-human IgG F(ab')$_2$ antibody (Serotech) is diluted at 1:20 with PBS, and 20 $\mu$l of the resultant antibody is put on the slide and reacted at room temperature for 30 minutes in a humidified chamber. After the reaction is completed, the resultant substance is washed with PBS. The washed substance is embedded with glycerol diluted to 1:9 with PBS and observed with a fluorescent microscope. The observation results obtained in this manner are shown in Table 1. Among the 35 ulcerative colitis patients, 24 patients had ANCA (the percentage of the positive components: 69%; see Table 1).

Regarding the stain pattern obtained by the indirect immunofluorescence assay, the anti-neutrophil cytoplasmic antibodies (ANCA) of the 24 positive patients mostly had pANCA (pANCA for 22 patients; nuclear-ANCA for 2 patients; see Table 1). The two patients exhibiting nuclear-ANCA are patient Nos. 24 and 25 in Table 3 shown below.

phosphotase (ALP)-tagged ovine anti-human IgG antibody (Immunotech S.A.) was diluted 1000-fold with 5% BSA/PBS, added to each well and reacted at room temperature for 24 hours. After the reaction was completed, each well was washed 5 times with 1% BSA/0.5% Tween20/PBS. After the washing, 100 $\mu$l of 10% solution of p-nitrophenyl phosphate (final concentration: 5 mg/ml) in diethanolamine (diethanolamine 50 ml+distilled water 450 ml) was added and color-developed at room temperature for 30 minutes. After the color development, the absorbance at 405 nm was measured.

According to this method, the anti-MPO antibody was not detected in any of the samples. Among the 24 patients who were found to be positive by the indirect immunofluorescence assay, 9 patients were positive regarding the anti-CaG antibody and 3 patients were positive regarding the anti-LF antibody. For the other 12 patients, the antigen responsible for the positive reaction was not specified (see Tables 2 and 3 below).

Example 3

Screening of Antigen to Anti-neutrophil Cytoplasmic Antibody (ANCA)

Regarding the 24 ANCA-positive patients, Western blotting was performed using the neutrophil lysate.

Peripheral blood was sampled from healthy persons, and neutrophil fractions were prepared by the centrifugation using the Ficoll-Hypaque technique. $10^6$ neutrophils were suspended in 8 $\mu$l of PBS per well. Then, 2 $\mu$l of sample buffer (0.2M Tris-HCl pH6.8/10% SDS/25%

TABLE 1

ANCA detected in ulcerative colitis and Crohn's disease patients by the indirect immunofluorescence assay

| Patient | Number of patients | Percentage of positive patients(%) | Staining pattern | | | Titer |
| --- | --- | --- | --- | --- | --- | --- |
| | | | Perinuclear | Cytoplasmic | Nuclear | |
| Ulcerative colitis | 35 | 24(59) | 22 | 0 | 2 | 1/10–1/320 |
| Crohn's disease | 10 | 6(50) | 2 | 4 | 0 | 1/10–1/40 |
| Healthy | 39 | 0(0) | | | | |

Example 2

Study on Known Antigens to ANCA

Antigens to ANCA were studied for the 35 ulcerative colitis patients.

Five micrograms /ml of myeloperoxidase (MPO; Elastin Products), 5 $\mu$g/ml of cathepsin G (CaG; INC Biochemical) and 10 $\mu$g/ml of lactoferrin (LF; Sigma) were prepared, injected into 96-well microtiter plates in the quantities of 50 $\mu$l/well, 50 $\mu$l/well and 100 $\mu$l/well, respectively, and stored at 4° C. overnight to coat the wells. After the coating, the solution was removed, and 5% BSA (bovine fetus serum)-containing PBS (5% BSA/PBS) was added to each well and reacted for 30 minutes. Then, 5% BSA/PBS was removed. The serum obtained from the patients was diluted 10-fold using 5% BSA/PBS, added to the microtiter plates, and reacted at room temperature for 24 hours. The reaction liquid was removed, and each well was washed 5 times with 1% BSA/PBS/0.5% Tween20. After the washing, alkali 2-mercaptoethanol/25% glycerol/0.01% BPB) was added and immediately boiled for 10 minutes, thereby obtaining an antigen solution. Electrophoresis of the antigen solution was performed using SDS-polyacrylamide gel (SDS-PAGE). After the electrophoresis, the resultant substance was transferred to Immobilon membrane (Millipore) in a usual manner and reacted for 2 hours after skim milk was added in order to block non-specific bonding. Serum obtained from the patients in an amount of 320 $\mu$l was applied to ProCep A (10 ml bed volume; Bio Processing). Then, IgG fractions were eluted using 0.1M-glycine (pH3.0) and purified, thereby obtaining a 20 mg/ml solution of IgG. The above-prepared Immobilon membrane and 1 ml of the IgG solution diluted 8-fold with 5% skim milk were reacted at 4° C. overnight. After being washed, the resultant substance was further reacted with 13 $\mu$g/ml of myeloperoxidase-bound anti-human IgG antibody (Kirkegaard & Perry Laboratories, Inc.). The resultant substance was chemically emitted with an ECL kit (Amersham), and the band was detected. The results are shown in Tables 2 and 3.

TABLE 2

| Patient No. | IIF | MPO | CaG | LF | 28 kDa, antigen, etc. | Refractory type |
|---|---|---|---|---|---|---|
| 1 | + | − | − | − | + | + |
| 2 | + | − | − | + | − | − |
| 3 | + | − | − | − | − | − |
| 4 | + | − | + | − | + | + |
| 5 | + | − | − | − | − | − |
| 6 | + | − | + | − | + | + |
| 7 | + | − | − | + | − | − |
| 8 | + | − | + | − | +(39.5 kDa) | + |
| 9 | + | − | − | − | − | − |
| 10 | + | − | − | − | − | − |
| 11 | + | − | − | − | +(47 kDa) | − |
| 12 | + | − | − | − | − | − |
| 13 | + | − | − | − | − | − |
| 14 | + | − | + | − | + | − |
| 15 | + | − | − | − | +(44 kDa) | − |
| 16 | + | − | − | − | − | − |
| 17 | + | − | + | − | + | + |
| 18 | + | − | − | − | − | − |
| 19 | + | − | − | − | − | − |
| 20 | + | − | + | − | + | − |

In the table, "+" indicates positive reactivity or refractory type.

TABLE 3

| Patient No. | IIF | MPO | CaG | LF | 28 kDa, antigen, etc. | Refractory type |
|---|---|---|---|---|---|---|
| 21 | + | − | + | − | + | + |
| 22 | + | − | − | + | − | + |
| 23 | − | − | + | − | − | − |
| 24 | + | − | + | − | +(50 kDa) | − |
| 25 | + | − | − | − | − | − |
| 26 | − | − | − | − | − | − |
| 27 | − | − | − | − | − | − |
| 28 | − | − | − | − | − | − |
| 29 | − | − | − | − | − | − |
| 30 | − | − | − | − | − | − |
| 31 | − | − | − | − | − | − |
| 32 | − | − | − | − | − | − |
| 33 | − | − | − | − | − | − |
| 34 | − | − | − | − | − | − |
| 35 | − | − | − | − | − | − |

In the table, "+" indicates positive reactivity or refractory type.

As a result, the sera of 11 patients among the 24 patients who were positive regarding the anti-neutrophil cytoplasmic antibody (ANCA) were found to contain an antigen capable of binding with either one of the 28/39.5/44/47/50/58 kDa bands. Especially, the sera of seven patients among the 11 patients were confirmed to contain a substance capable of binding with the 28 kDa band. Five out of seven patients containing the 28 kDa band were diagnosed to have refractory ulcerative colitis (see FIG. 1).

In the sera obtained from the ulcerative colitis patients in which ANCA were not indicated by the indirect immunofluorescence assay (ANCA-negative patients), no antibody capable of binding with 28 kDa was found. In the sera of the Crohn's disease patients used as the control, no antibody capable of binding with 28 kDa was found.

These results are summarized as follows. Among the 35 ulcerative colitis patients, 24 patients were ANCA-positive in accordance with the indirect immunofluorescence assay, and 11 patients were found to have an antigen capable of binding with ANCA by Western blotting. (All the 11 patients were ANCA-positive in accordance with the indirect immunofluorescence assay.) Among the 35 patients, 7 patients had refractory ulcerative colitis. Six out of the 7 patients were found to have an antigen capable of binding with ANCA by Western blotting, and the 28 kDa band was found in 5 out of the 6 patients. No positive band was found in the serum of the Crohn's patients used as the control (see FIG. 1).

These experiment results suggest that expression of an antibody against the neutrophil 28 kDa antigen can be a marker for predicting the seriousness (refractory type) of the ulcerative colitis and demonstrates the importance of isolation analysis of the antigen and the importance of developing a detection system for a simple antibody using an isolated antigen.

Example 4

Confirmation of Existence of 28 kDa and 29 kDa Antigens in HL-60 Cells

Figure 2:
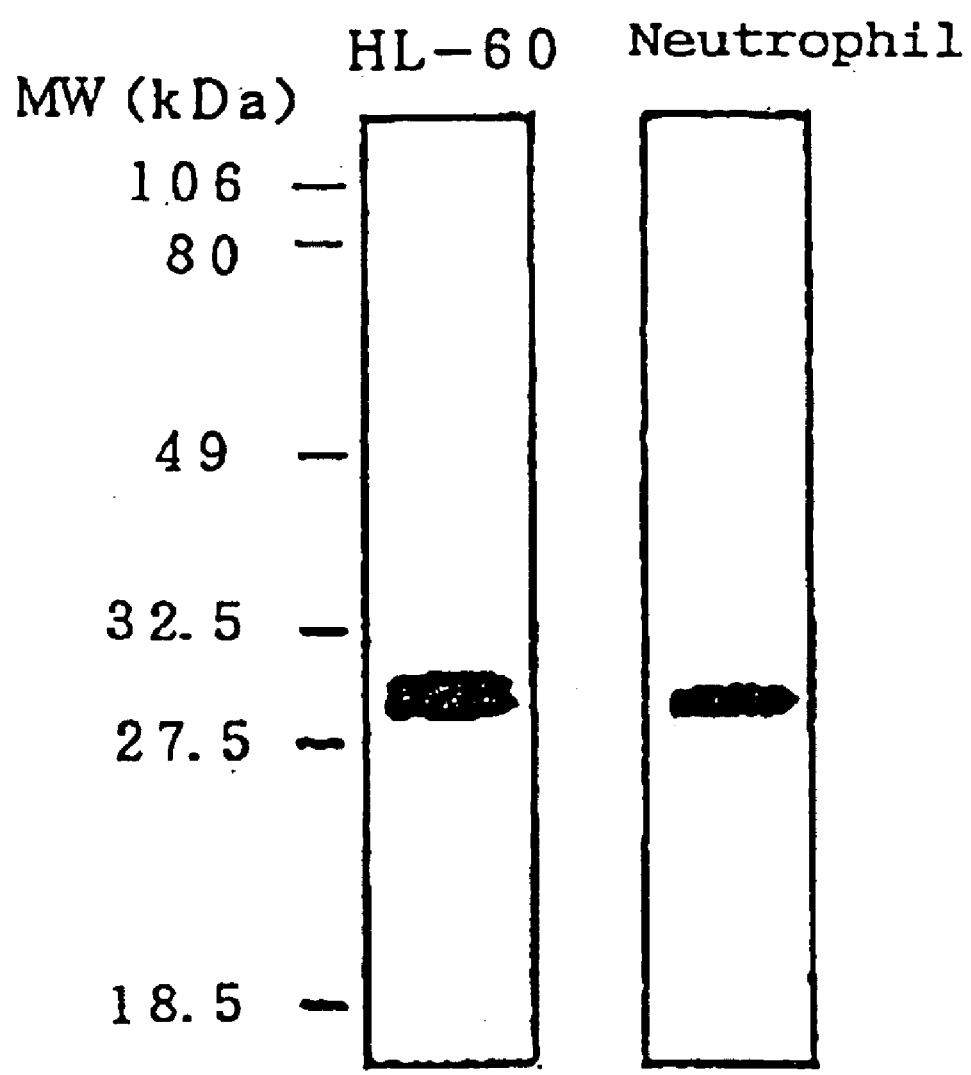
FIG. 2 is the results of Western blotting performed using cytoplasm lysates of neutrophil and HL-60 as antigens and also using serum of 28 kDa antigen-positive patients as a probe.

HL-60 cell lines, which are neutrophil-type cells derived from premyelogenetic leukemia, were cultured in a RPMI1640 medium containing 5% FCS added thereto, and neutrophil lysate was created in the same method as in Example 3. Using the lysate, Western blotting was performed in the same manner as in Example 3. The results are shown in FIG. 2 together with the results obtained from the positive control using the neutrophil lysate. Based on the results, the 28 kDa antigen capable with binding with the antibody fraction obtained from the ulcerative colitis patients was confirmed to exist. The 28 kDa band was detected as a thick band, which suggests that the 29 kDa antigen exists proximate to the 28 kDa antigen.

Example 5

Purification of 28 kDa and 29 kDa Antigens from HL-60 Cells

Figure 3:
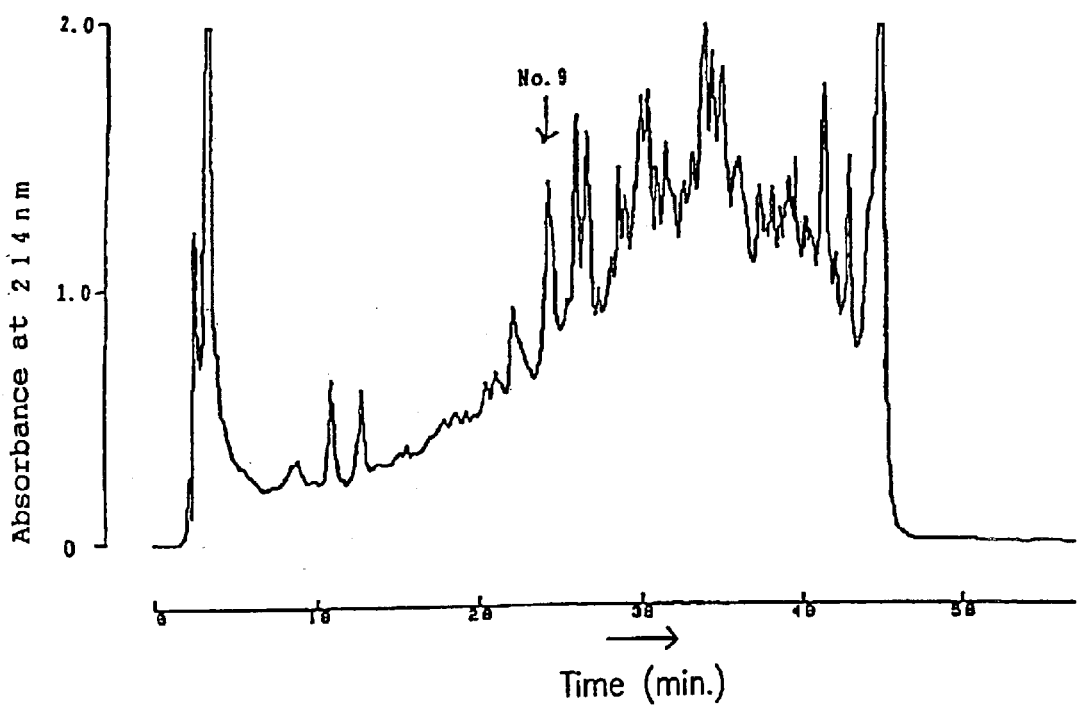
FIG. 3 shows a pattern obtained with HPLC during isolation of an antigen from the HL-60 cell, in which the No. 9 peak includes the 28 kDa and 29 kDa antigens.
Figure 4:
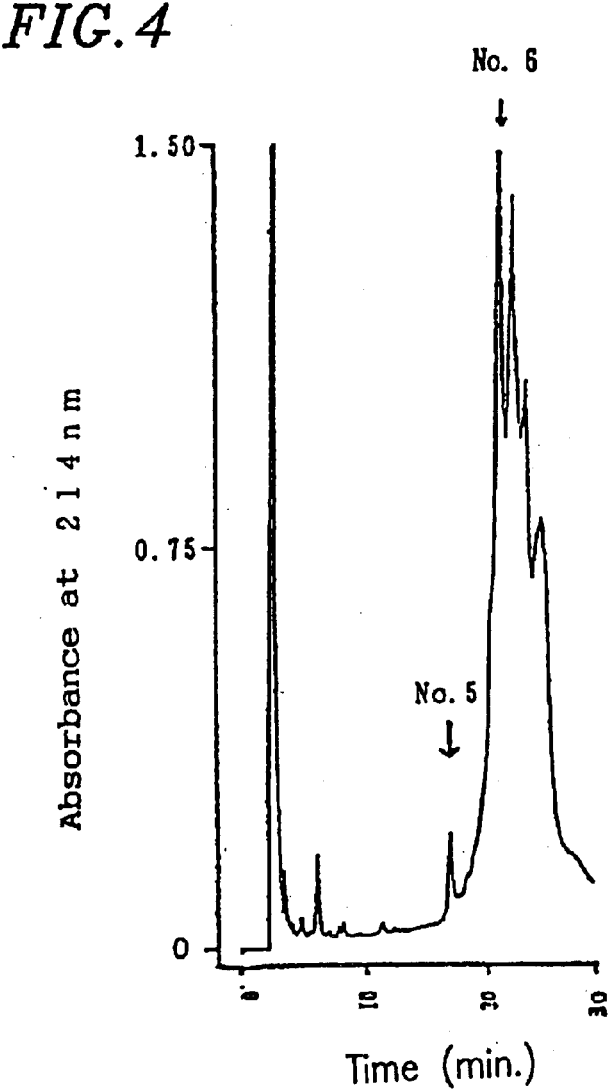
FIG. 4 shows a pattern obtained with HPLC during isolation of an antigen from the HL-60 cell, in which the No. 5 peak includes the 28 kDa antigen and the No. 6 peak includes the 29 kDa antigen.
Figure 5:
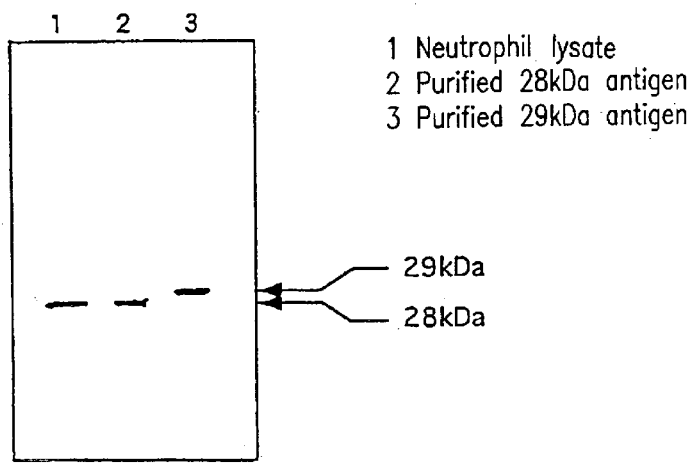
FIG. 5 shows a pattern obtained by Western blotting with the purified 28 kDa antigen (lane 2) and the purified 29 kDa antigen (lane 3)

The HL-60 cells which were confirmed to contain the antigens in Example 4 were cultured in a RPMI1640 medium containing 5% FCS added thereto. When $1 \times 10^5$/ml cells in a 75 cm$^2$ flask were increased to $2 \times 10^6$/m, the cells were centrifuged so that the total number of the cells were $2 \times 10^8$, thereby recovering the cells. Ten milliliters of 6M guanidine hydrochloride were added to the resultant substance to be dissolved, sonic treatment (USP600, Shimadzu) was performed for 10 minutes. Such treatment completely dissolved the cells. After distilled water in the same amount as the resultant solution was added, centrifugation was performed for 30 minutes at 80,000×g and supernatant was recovered. The supernatant was placed in an Amicon ultrafiltration device (Amicon) equipped with YM3 (Amicon), which is a membrane having a molecular cut of 3,000. Filtration was performed while PBS was added, and then the resultant substance was concentrated, thereby finally obtaining 4 ml of PBS solution. The PBS solution was centrifuged for 30 minutes at 80,000×g to remove the precipitate, thereby recovering supernatant. The recovered supernatant was used as the antigen-containing sample, and 28 kDa and 29 kDa fractions were separated from the sample using HPLC. Using a YMC-pack protein RP column (YMC), proteins were eluted from acetonitrile having a concentration of 16% by 48% concentration gradient. The results are shown in FIG. 3. No. 9 peak fraction in FIG. 3 was collected and lyophilized. The lyophilize sample was re-dissolved in PBS. Using the YMC-pack protein RP column (YMC) again, proteins were eluted from acetonitrile having a concentration of 24% by 36% concentration gradient. As the HPLC system, the LC-7A system (Shimadzu) was used. The results are shown in FIG. 4. No. 5 and No 6 peak fractions were collected and lyophilized. The lyophilizate was electrophoresed on SDS-PAGE, and transferred to a PVDF membrane (Amersham) by Western blotting. After staining with Ponceau S, the 28 kDa and 29 kDa bands were cut out and recovered. The results of Western blotting performed on the purified antigens are shown in FIG. 5. In the SDS-PAGE in the purified antigens, the two types of proteins were separated from each other and were identifiable. Since both types of proteins reacted with the sera from the patients, it is assumed that the proteins cannot be separated from each other in the SDS-PAGE from a cell lysate because the molecular weights are proximate to each other or that neutrophils cannot be detected because the quantity of the neutrophils contained in the 29 kDa antigen is excessively small.

Example 6

Partial Amino Acid Sequencing and Homology Analysis

The membrane containing the 28 kDa and 29 kDa recovered in Example 5 was dried and then used for amino acid sequencing. The amino acid sequencing was performed using PPSQ-10, which is an automatic protein sequencer produced by Shimadzu. As a result, 32 amino acids from the N-terminal were sequenced for the 28 kDa band. The sequence was as follows.

Gly Lys Gly Asp Pro Asn Lys Pro Arg Gly Lys Met Ser Ser Tyr Ala Phe Phe Val Gln Thr Xaa Arg Glu Glu His Lys Lys Lys His Pro Asp (SEQ NO:12)

As a result of a similar analysis of amino acid sequences of the 29 kDa band, 32 amino acids from the N-terminal were sequenced. The sequence was as follows.

Gly Lys Gly Asp Pro Lys Lys Pro Arg Gly Lys Met Ser Ser Tyr Ala Phe Phe Val Gln Thr Xaa Arg Glu Glu His Lys Lys Lys His Pro Asp (SEQ NO:13)

Example 7

Homology Analysis of Partial Amino Acid Sequence

Homology analysis of the amino acid sequences obtained in Example 6 was performed. Using the BLAST program of Altschul, S. F. et al. (J. Mol. Biol. 205, 403–410, 1982), a homology search was performed for all the amino acid sequences included in the known data PIR. As a result, 31 out of 32 amino acids of the 29 kDa antigen matched with those of non-histone nucleic protein HMG-1 (Reeck, G. R., Nucleic Acids Res. 17, 1197–1214, 1989), and 31 of 32 amino acids of the 28 kDa antigen matched with those of HMG-2 (Majumdar, A. et al., Nucleic Acids Res. 19, 6643, 1991). The 22nd cystine could not identified in both of the antigens. Since cystine is not detected unless modifying a thiol group, the 22nd amino acid is considered to be cystine. In consideration of this assumption and the molecular weight measured by SDS-PAGE, the 28 kDa and 29 kDa antigens were identified as HMG-2 and HMG-1, respectively.

Example 8

Absorption Test of Antibody of the Patients by HMG Antigen

Figure 6:
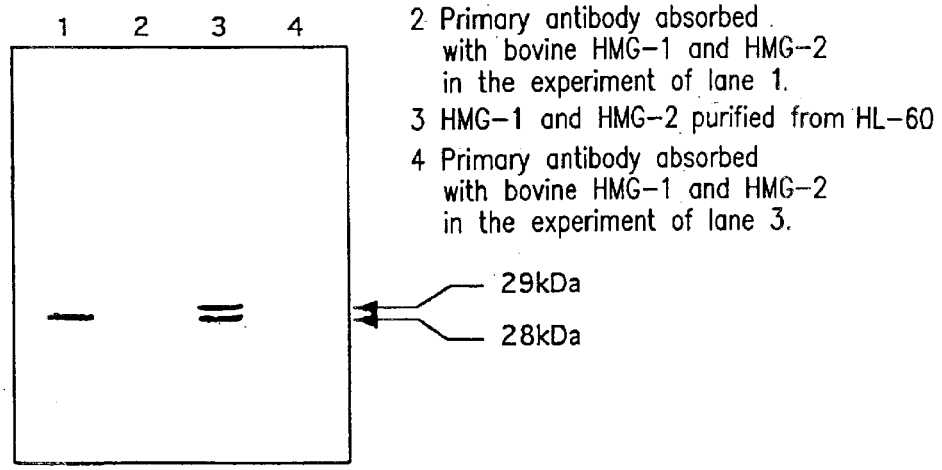
FIG. 6 shows the results of absorption test of antibody from the patients by HMG-1 and HMG-2, in which bands (1, 3) are detected with the positive control but bands (2, 4) are not present when the antibodies are absorbed.

Each of the HMG-1 and HMG-2 antigens purified in Example 5 and the neutrophil lysate were treated with SDS-PAGE in the same manner as in Example 3, and the resultant substance was transferred to the Immobilon membrane. Used as a primary antibody was an antibody solution obtained by mixing IgG (0.024 mg/ml) obtained and purified from HMG antigen-positive ulcerative colitis patients and bovine HMG-1/2 mixture (0.5 mg/ml) at a ratio of 1:2 and reacting the substances at 4° C. overnight. As in Example 3, the antibody solution was washed, and reacted with a secondary antibody. Detection was performed by ECL kit. As a result, the 28 kDa and 29 kDa bands and the neutrophil 28 kDa band were extinguished in the experiment result obtained using the antibody absorbed with the bovine HMG-1/2 mixed solution (see FIG. 6). Based on these results also, the 29 kDa and 28 kDa antigens are considered to be HMG-1 and HMG-2, respectively.

Example 9

Preparation of HMG-1 and HMG-2 Fractions from Human Thymus Tissue

Figure 7:
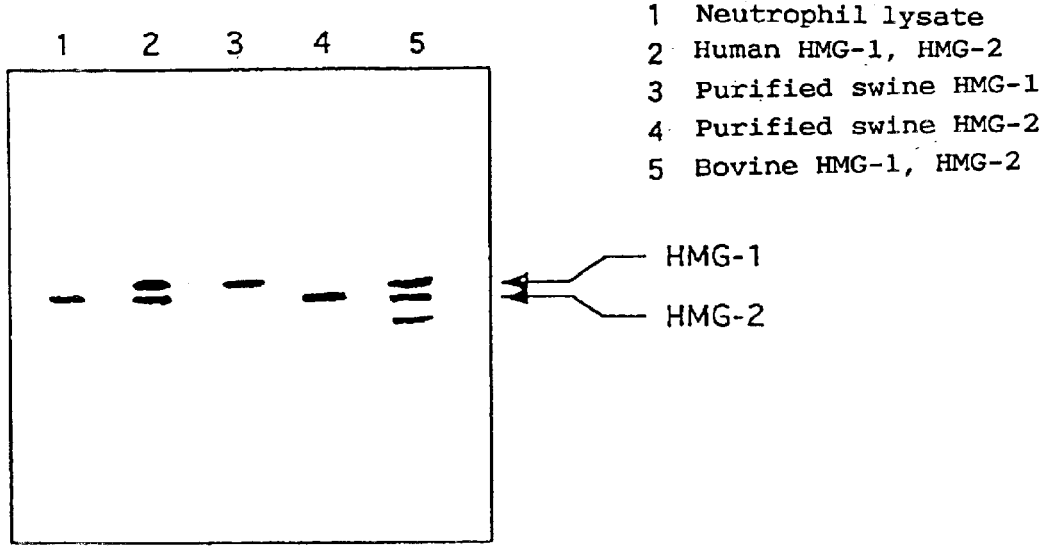
FIG. 7 shows the results of Western blotting performed on a mixture of HMG-1 and HMG-2 prepared from human thymus tissue, a mixture of HMG-1 and HMG-2 prepared from porcine thymus tissue, and a commercially available mixture of HMG-1 and HMG-2 of bovine thymus tissue; in which all the human, porcine and bovine HMG antigens reacted with serum from refractory ulcerative colitis patients, 15% polyacrylamide being used for SDS-PAGE only in this example.

HMG-1 and HMG-2 can be prepared in a simple manner in accordance with the methods described in the above-mentioned documents from the human, porcine or bovine thymus tissue. Thymus tissue of a child (13 g) was cut into thin strips and suspended in 30 ml of 0.075M NaCl/0.025M EDTA (pH7.5). Then, the cells were destroyed for 2 minutes in ice water using a Polytron homogenizer (speed 10, 2 minutes). By performing centrifugation at 4° C. for 30 minutes at 2,000×g, precipitate containing chromatin was recovered. This operation was repeated 4 more times (except that homogenization was performed for 1 minute), thereby suspending the precipitate in 30 ml of 0.35M NaCl (pH7). The suspension was treated by the homogenizer (speed 5, 1 minute), thereby freeing HMG bound to chromatin. This operation was repeated 2 more times to prepare 90 ml of solution. By performing centrifugation at 4° C. for 30 minutes at 2,000×g, insoluble substances were removed. Trichloroacetic acid was added to the resultant supernatant to prepare a 2% solution of trichloroacetic acid. The solution was left at 4° C. for 1 hour, and then insoluble substances other than HMG-1 and HMG-2 were precipitated. Supernatant was recovered by centrifugation (4° C., 2000×g, 30 minutes), and 2-mercaptoethanol was added so as to obtain a final concentration of 0.01M. 30% ammonia was added in an amount of 1.5 ml, and 300 ml of acetone was immediately added and stirred. The resultant substance was left at 4° C. overnight. The precipitated HMG-1 and HMG-2 were recovered by centrifugation, washed with 90% acetone and dried. This fraction was dissolved in 6M guanidine hydrochloride, and substitution into PBS by dialysis and concentration were performed, thereby obtaining HMG-1 and HMG-2 fractions. The HMG-1 and HMG-2 fractions reacted with an antibody of the ulcerative colitis patients by Western blotting (see FIG. 7). Commercially available bovine HMG-1 and HMG-2 (Wako Pure Chemical) also reacted with an antibody from the ulcerative colitis patients (see FIG. 7). Accordingly, HMG-1 and HMG-2 are considered as antigens from the ulcerative colitis patients.

Example 10

Purification of Porcine Thymus-derived HMG-1 and HMG-2

Figure 8:
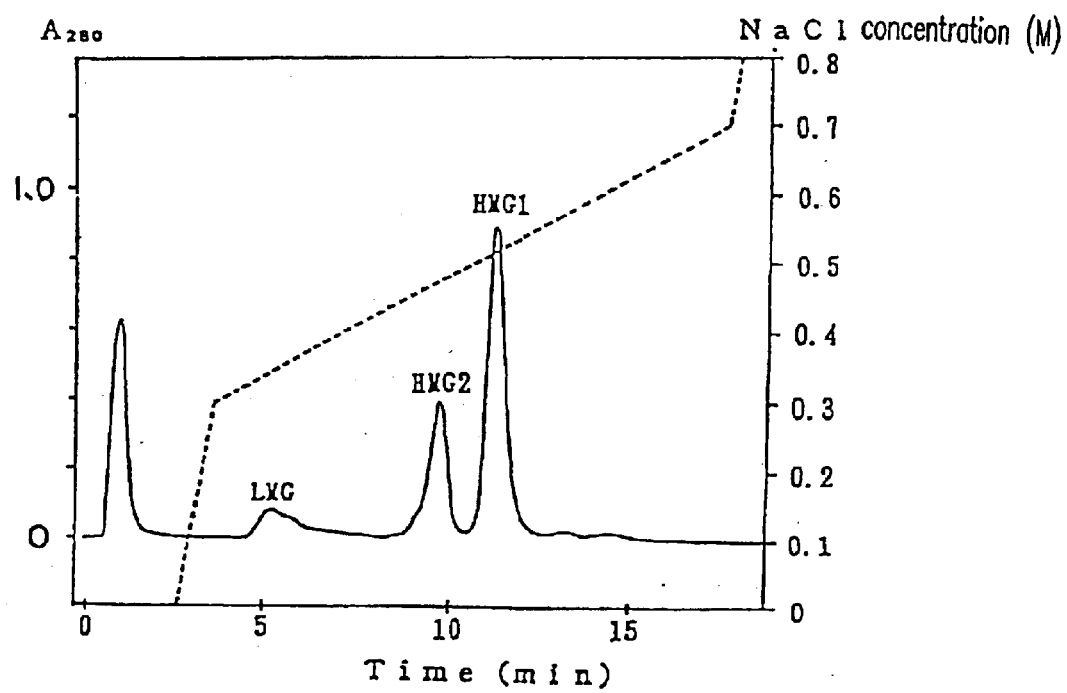
FIG. 8 shows purification of HMG-1 and HMG-2 from porcine thymus.

Porcine thymus-derived HMG-1 and HMG-2 were purified in accordance with the method of M. Yoshida and K. Shimura (J. Biochem., Tokyo, 95, 117–124, 1980) and Y. Adachi et al. (J. Chromatogr., 530, 39–46, 1992). The purification method will be described briefly. The chromatin fraction obtained in the same manner as in Example 9 was suspended in 0. 35M NaCl (pH7)/1 mM PMSF and homogenized by the Potter-Elvehjem PTFE homogenizer. By performing centrifugation for 20 minutes at 5,000×g, supernatant was recovered. This operation was repeated twice and the resultant supernatants were mixed. Trichloroacetic acid was added to this fraction to prepare a 2% solution of trichloroacetic acid. The solution was treated with centrifugation to remove the precipitate. Trichloroacetic acid was added to the supernatant to prepare a 10% solution of trichloroacetic acid solution. The deposited precipitate containing HMG-1 and HMG-2 was recovered by centrifugation. The precipitate was dissolved in 3 ml of 10 mM Tris-HCl (pH7.8) and applied to Mono Q column (5×50 mm, Pharmacia), which had been washed and equilibrated with the same buffer solution, for separation (using the FPLC system produced by Pharmacia). The elution was performed by linear concentration gradient from 0 to 1M of NaCl. FIG. 8 shows the elution pattern. According to this fraction method, HMG-1 and HMG-2 were obtained at a purity of about 95% or higher.

The obtained HMG was confirmed to react with the antibody from the patients by Western blotting. The HMG-1 fraction was confirmed not to contain HMG-2 mixed therein, and the HMG-2 fraction was confirmed not to contain HMG-1 mixed therein (see FIG. 7).

Example 11

Figure 9:
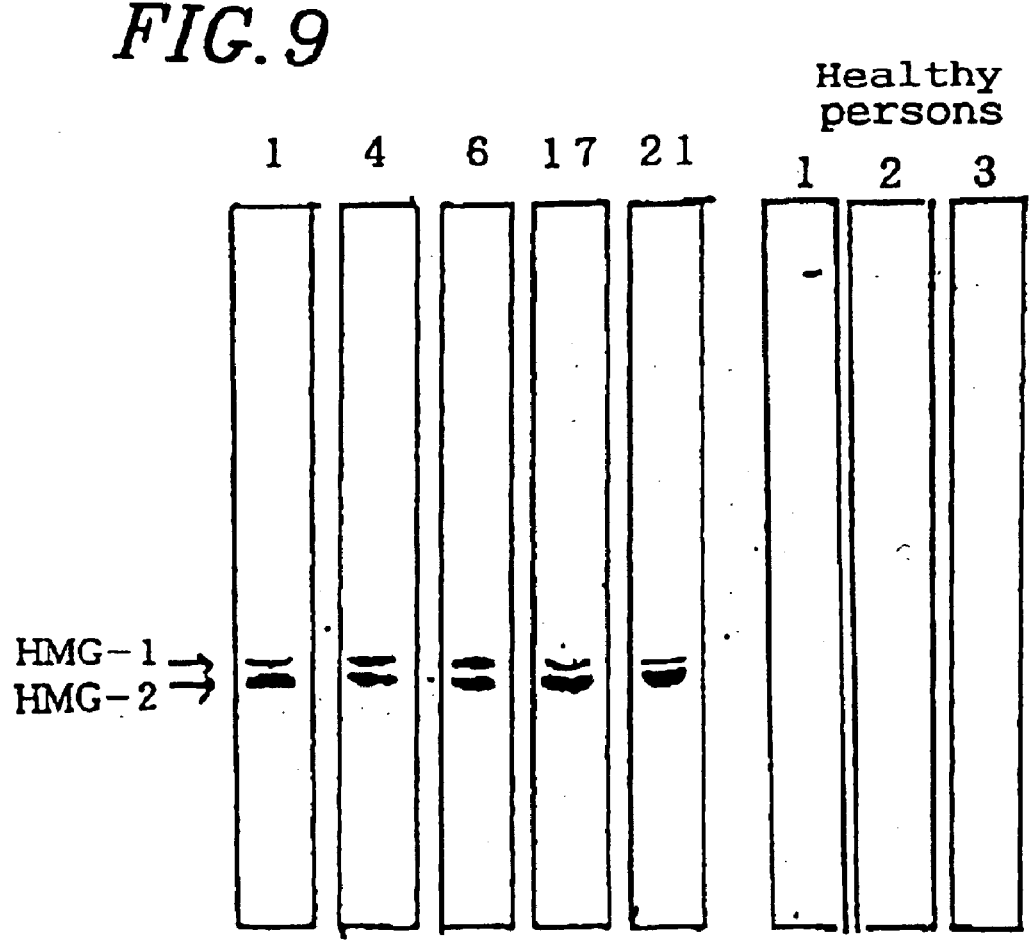
FIG. 9 shows the results of Western blotting performed using as an antigen a mixture of bovine HMG-1 and bovine HMG-2 from five ulcerative colitis patients and three healthy persons.

Detection of Anti-HMG-1 Antibody and Anti-HMG-2 Antibody in UC Patient Serum by Western Blotting Western blotting was performed using a bovine HMG-1 and HMG-2 mixture (available from Wako Pure Chemical) as an antigen. A mixture of bovine HMG-1 (0.5 μg) and bovine HMG-2 (0.5 μg) was dissolved in a sample buffer (Example 3), and heat-treated in a usual manner, thereafter SDS-PAGE was performed. After the SDS-PAGE was completed, the antigens were transferred to a PVDF membrane and reacted with the UC patient serum and with HRP-tagged anti-human IgG antibody in this order. Detection was performed by ECL kit. The results are shown in FIG. 9. These results demonstrate that anti-HMG-1 antibody and anti-HMG-2 antibody exist in the UC patient serum.

Example 12

Figure 10:
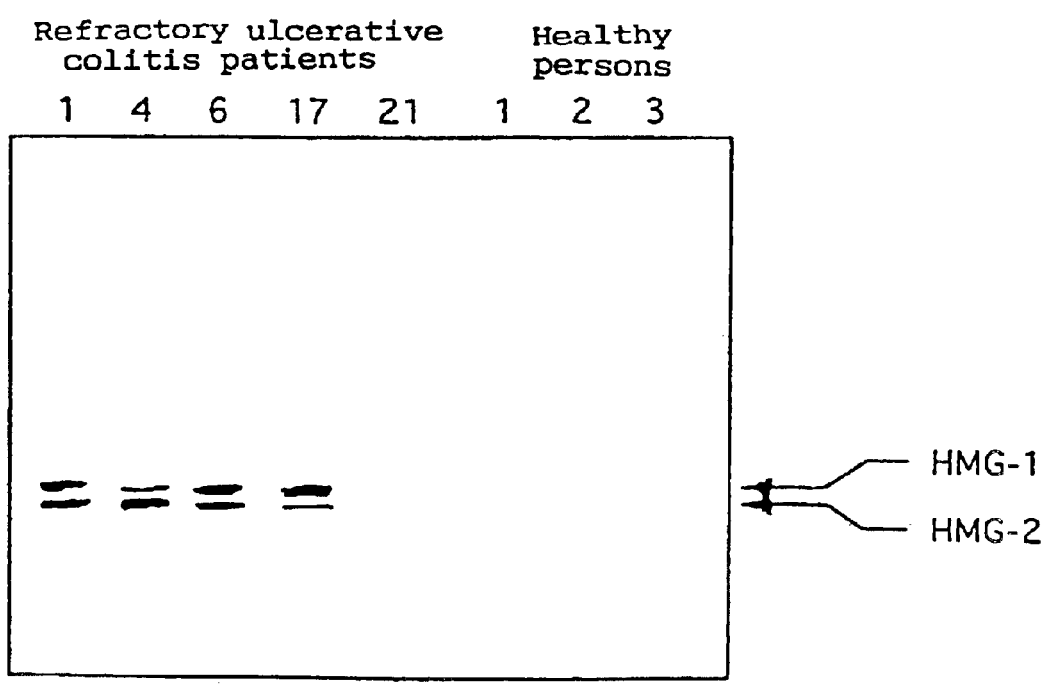
FIG. 10 shows the results of Western blotting performed using as an antigen a mixture of porcine HMG-1 and porcine HMG-2 from five ulcerative colitis patients and three healthy persons.

Detection of Anti-HMG-1 Antibody and Anti-HMG-2 Antibody in Refractory Ulcerative Colitis Patient Serum by Western Blotting Western blotting was performed using a porcine HMG-1 and HMG-2 mixture as an antigen. A mixture of porcine HMG-1 (0.5 μg) and porcine HMG-2 (0.5 μg) was dissolved in a sample buffer (Example 3), and heat-treated in a usual manner, thereafter SDS-PAGE was performed. After the SDS-PAGE was completed, the resultant substance was transferred to a PVDF membrane and reacted with the serum from 5 28 kDa-positive refractory ulcerative colitis patients and with HRP-tagged anti-human IgG antibody in this order. Detection was performed by ECL kit. As a result, it was found that four out of the five refractory ulcerative colitis patients were positive and 1 patient was 28 kDa-positive but the antigen of this patient was not HMG-1 or HMG-2 (see FIG. 10). These results demonstrate that anti-HMG-1 antibody and/or anti-HMG-2 antibody exists in the refractory ulcerative colitis patient serum.

Example 13

Measurement of Anti-HMG-1 Antibody and Anti-HMG-2 Antibody by an ELISA Assay

In each well of a 96-well ELISA plate (Nunc), 5 μg/ml of bovine HMG-1 and HMG-2 were each added in quantities of 50 μl and left in a stationary state at 4° C. for 24 to 36 hours. After excess antigen was removed, 200 μl of 5% BSA was added and left in a stationary state for 30 minutes or longer for performing blocking. Serum from the patients diluted 40-fold or 80-fold with 5% BSA was added in a quantity of 50 μl and left in a stationary state at room temperature for 2 hours. After the resultant substance was washed 5 times with 0.05% Tween/0.02% azide/PBS (washing liquid), 100 μl of alkali phosphotase-tagged goat anti-human IgG (F(ab')$_2$) (available from Funakoshi) diluted 1000-fold was added and reacted at room temperature for 2 hours. After the resultant substance was washed 5 times with the washing liquid, 100 μl of 0.1% p-nitrophenyl phosphate, disodium (pNPP; Sigma) solution (10% diethanolamine solution) was added and reacted at room temperature for 20 to 25 minutes. The absorbance at 405 nm was measured.

Figure 11:
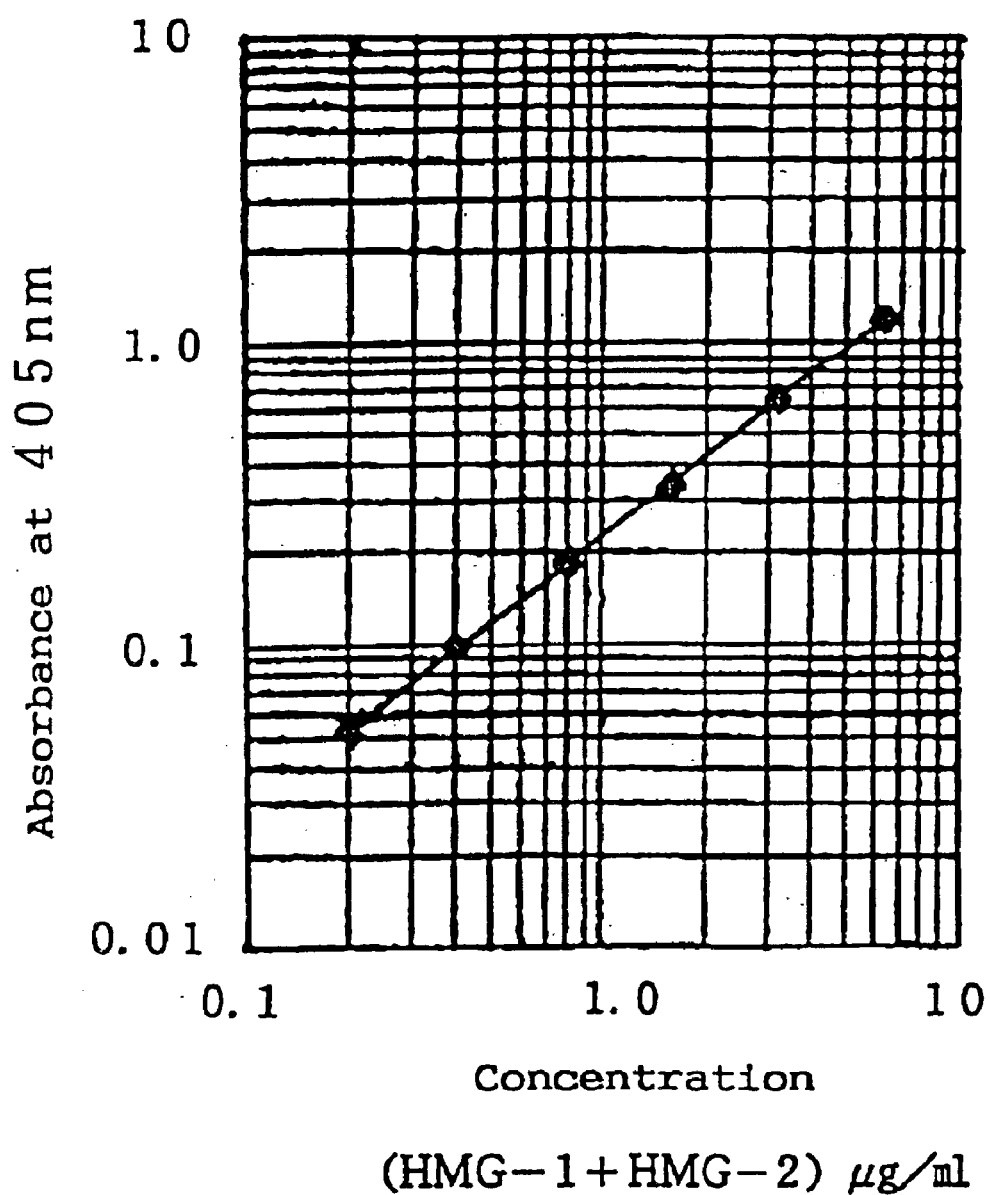
FIG. 11 shows a dosage-dependent line showing the measurement results on the serum of positive patients performed by an ELISA assay.

FIG. 11 shows a calibration curve of the positive control. Based on the calibration curve, it has been found that measurement for anti-HMG-1 antibody and/or anti-HMG-2 antibody can be performed by an ELISA assay using bovine HMG-1 and HMG-2. As a result of the measurement of the serum of 68 ulcerative colitis patients, 20 patients were positive (29.4%), which is significantly higher than 7.1% (4/20 subjects) among the healthy persons. The value of mean+3SD or higher of the healthy control was set as positive. Regarding the ulcerative colitis patients, 5 out of 7 refractory ulcerative colitis patients were positive (71.4%), which is quite high.

Example 14

Measurement of Anti-HMG-1 Antibody and Anti-HMG-2 Antibody by an ELISA Assay

Figures 3, 12:
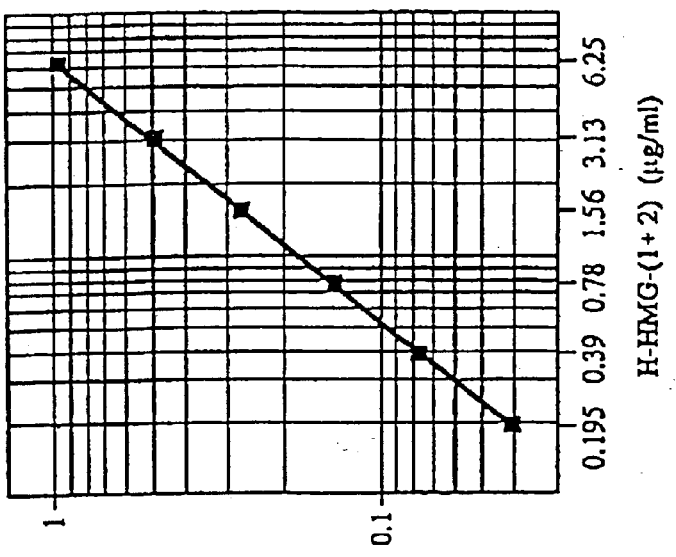
FIG. 12 shows measurement results on an anti-HMG-1 antibody and an anti-HMG-2 antibody performed by an ELISA assay, in which dosage-dependent lines are obtained with porcine HMG-1 (FIG. 12-1), porcine HMG-2 (FIG. 12-2), and a mixture of human HMG-1 and human HMG-2 (FIG. 12-3)
Figures 2, 12:
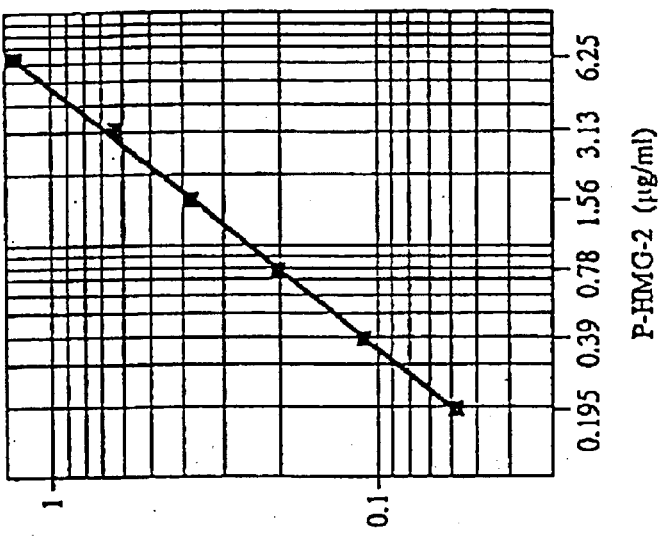
Figures 1, 12:
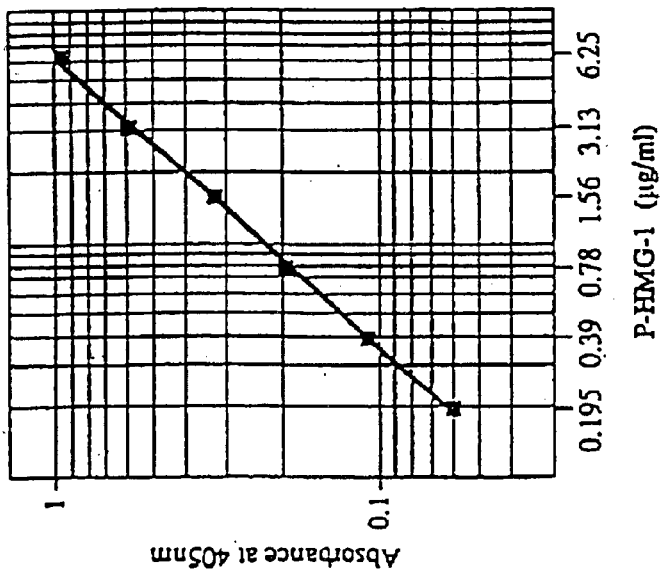

ELISA assay was performed using porcine HMG-1, porcine HMG-2 or a mixture of human HMG-1 and human HMG-2 as an antigen. In each well of a 96-well Maxisorp plate (Nunc), 50 μl of porcine HMG-1 or HMG-2 diluted from 6.25 μg/ml in a stepped manner or 50 μl of human HMG-1 or HMG-2 (equivalent mixture) diluted from 6.25 μg/ml in a stepped manner was added and left in a stationary state at 4° C. for 24 to 36 hours. After excess antigen was removed, 200 μl of 5% BSA was added and left in a stationary state for 30 minutes or longer for performing blocking. Serum from the anti-HMG-1 antibody- and/or anti-HMG-2 antibody-positive refractory ulcerative colitis patients was set as the standard serum. Such serum was diluted 40-fold with 5% BSA and added in an amount of 50 μl and left in a stationary state at room temperature for 2 hours. After the resultant substance was washed 5 times with 0.05% Tween/0.02% azide/PBS (washing liquid), 100 μl of alkali phosphotase-tagged goat anti-human IgG (F(ab')$_2$) (Immunotech S.A.) diluted 1000-fold was added and reacted at room temperature for 2 hours. After each well was washed 5 times with the washing liquid, 100 μl of 0.1% p-nitrophenyl phosphate (Sigma) solution (10% diethanolamine solution) was added and reacted at room temperature for 20 to 25 minutes. The absorbance at 405 nm was measured. FIG. 12 shows calibration curves of the positive controls. By all three types of ELISA assays, dosage-dependent straight lines were obtained. Based on these calibration curves, it was found that measurement for anti-HMG-1 antibody and/or anti-HMG-2 antibody can be performed by an ELISA assay using porcine HMG-1 (FIG. 12-1), porcine HMG-2 (FIG. 12-2) or a mixture of human HMG-1 and HMG-2 (FIG. 12-3). The calibration curves also suggest that the concentration of 5 μg/ml realizing an absorbance of about 1.0 can be appropriately used for measurement.

Example 15

Measurement of Anti-HMG-1 Antibody and Anti-HMG-2 Antibody in the Case of AIH

Using an ELISA system, measurement for the antibodies of AIH patients, hepatitis B patients, and hepatitis C patients was performed. Sera from 33 healthy persons were used as the control. As an antigen, 5 μg/ml of each of porcine HMG-1 and porcine HMG-2 was used. The standard serum was diluted 40-fold and used for measurement. A value obtained by subtracting the absorbance of blank well containing no antigen from the absorbance of the standard serum was set as 100%. The ratio of the absorbance of the serum to be measured with respect to 100% was calculated and set as the value of the serum to be measured. The absorbance of the serum to be measured was obtained by subtracting the absorbance of blank well from the absorbance of the serum to be measured. When the value obtained from the serum diluted 40-fold was excessively high, the serum diluted 80-fold or more was used for measurement. The values exceeding the mean value of the healthy persons plus 2SD were set as positive.

In order to compare the percentage of anti-HMG-antibody-positive patients with the percentage of antinuclear antibody-positive patients, measurement on the antinuclear antibody by indirect immunofluorescence assay was performed on the same samples. The measurement was performed using the fluoro HEPANA test produced by MBL. For the AIH patients, the patients whose sera remained positive when being diluted 80-fold or more were labelled positive. For the hepatitis B and hepatitis C patients, the patients whose sera remained positive when being diluted 20-fold or more were labelled positive.

Table 4 shows the percentages of positive patients by antigen and by disease. The percentage was as high as 86% among the AIH patients and 27% for the hepatitis C patients. The percentage among the hepatitis B patients was 12%, which was not significantly different from the percentage among the healthy persons. Based on these results, it was found that diagnosis by exclusion is possible regarding hepatitis B and that the anti-HMG-1/2 antibody-positive patients have a high possibility of having AIH.

Among the AIH and hepatitis C patients, the percentage of anti-HMG-1/2 antibody-positive patients was higher than the antinuclear antibody-positive patients. Based on these results, it was found that AIH and hepatitis C can be diagnosed at a higher sensitivity with the anti-HMG-1/2 antibody than with the antinuclear antibody.

TABLE 4

| Disease | n | Percentage of positive patients (%) | | |
|---|---|---|---|---|
| | | HMG-1 | HMG-2 | HMG-1 + HMG-2 |
| Autoimmune hepatitis | 29 | 23 (79) | 24 (83) | 25 (86) |

TABLE 4-continued

| Disease | n | Percentage of positive patients (%) | | |
|---|---|---|---|---|
| | | HMG-1 | HMG-2 | HMG-1 + HMG-2 |
| Hepatitis B | 26 | 2 (8) | 2 (8) | 3 (12) |
| Hepatitis C | 30 | 8 (27) | 7 (23) | 8 (27) |
| Healthy persons | 31 | 0 (0) | 0 (0) | 0 (0) |

Example 16

Measurement of Anti-HMG-1 Antibody and Anti-HMG-2 Antibody in Each of Various Diseases Using an ELISA system, the following autoimmune disease patients and inflammatory disease patients were measured for antibodies: 50 rheumatoid arthritis patients, 47 systemic lupus erythematosus patients, 12 Sjögren's syndrome patients, 32 Behçet's disease patients, 15 polymyositis/dermatomyositis patients, 20 scleroderma patients, 41 primary biliary cirrhosis patients, 19 microscopic polyangiitis/polyarteritis nodosa patients, 62 ulcerative colitis patient, and 15 Crohn's disease patients. Sera from 33 healthy persons were used as the control. As an antigen, 5 μg/ml of each of porcine HMG-1 and HMG-2 was used. The standard serum was diluted 40-fold and used for measurement. On each plate, an antigen for calibration curves similar that in Example 12 was put separately from the antigen for serum to be measured. Using the standard serum (diluted 40-fold), measurement of the antigen for the calibration curve was performed parallel to the measurement of the antigen for the serum. Only when a linear calibration curve was obtained as shown in FIG. 11 from the plate, the measurement value of the sample in the plate was determined to be effective. A value obtained by subtracting the absorbance of blank well containing no antigen from the absorbance of the standard serum was set as 100%. The ratio of the absorbance of the serum to be measured with respect to 100% was calculated and set as the value of the serum to be measured. The absorbance of the serum to be measured was obtained by subtracting the absorbance of blank well from the absorbance of the serum to be measured. When the value obtained from the serum diluted 40-fold was excessively high, the serum diluted 80-fold or more was used for measurement. The values exceeding the mean value of the healthy persons plus 2SD were set as positive.

In order to compare the percentage of anti-HMG-antibody-positive patients with the percentage of antinuclear antibody-positive patients, measurement for antinuclear antibody was performed by indirect immunofluorescence assay on the same samples. The measurement was performed using the fluoro HEPANA test produced by MBL. Patients whose sera remained positive when being dilution 40-fold or more were labelled positive.

Table 5 shows the percentages of positive patients by antigen and by disease. FIG. 13 is a scatter diagram in accordance with disease obtained using HMG-1 as an antigen, FIG. 14 is a scatter diagram in accordance with disease obtained using HMG-2 as an antigen.

TABLE 5

| Disease | n | HMG-1 Number of positive patients | HMG-1 Percentage of positive patients (%) | HMG-2 Number of positive patients | HMG-2 Percentage of positive patients (%) | HMG-1 + HMG-2* Number of positive patients | HMG-1 + HMG-2* Percentage of positive patients (%) | Antinuclear antibody Number of positive patients | Antinuclear antibody Percentage of positive patients (%) |
|---|---|---|---|---|---|---|---|---|---|
| Rheumatoid arthritis (RA) | 50 | 31 | 62.0 | 17 | 34.0 | 34 | 66.0 | 29 | 58.0 |
| Systemic lupus erythematosus (SLE) | 47 | 29 | 61.7 | 15 | 31.9 | 31 | 66.0 | 39 | 83.0 |
| Sjögren's syndrome (SjS) | 12 | 9 | 75.0 | 1 | 8.3 | n.c.# | 75.0 | 9 | 58.3 |
| Multiple myositis/dermatomyositis (PM/DM) | 15 | 3 | 20.0 | 2 | 13.3 | n.c. | 20.0 | 10 | 15.6 |
| Scleroderma (PSS) | 20 | 11 | 55.0 | 2 | 10.0 | n.c. | 55.0 | 19 | 85.0 |
| Behcet's disease (Bechet) | 32 | 10 | 31.3 | 6 | 18.8 | 12 | 37.5 | 9 | 53.3 |
| Primary biliary cirrhosis (PBC) | 41 | 28 | 68.3 | 24 | 47.8 | 32 | 78.0 | 11 | 26.8 |
| Microscopic polyanteritis/polyarteritis nodosa (MPN/PN) | 19 | 8 | 42.1 | 3 | 15.0 | n.c. | 42.1 | 3 | 15.8 |
| Ulcerative colitis (UC) | 62 | 24 | 38.7 | 21 | 33.9 | 25 | 40.3 | 12 | 19.4 |
| Crohn's disease (CD) | 15 | 6 | 40.0 | 4 | 26.7 | 7 | 46.7 | 1 | 6.7 |
| Healthy control | 33 | 1 | 3.0 | 1 | 3.0 | 2 | 6.1 | 1 | 3.0 |

*: Number of patients who are anti-HMB-1 antibody-positive and also anti-HMG-2 antibody-positive
: No change In the primary biliary cirrhosis, ulcerative colitis and Behçet's disease patients, the percentage of the anti-HMG-1 antibody patients and the percentage of the anti-HMG-2 antibody patients were about the same. In the patients of the other seven diseases, the percentage of the anti-HMG-1 antibody patients was higher (Table 5), which indicates that the antigenicity of HMG-1 was stronger. Especially in the Sjögren's syndrome patients, the percentage of the anti-HMG-1 antibody patients was 66.7%, which is much higher than the percentage of the anti-HMG-2 antibody patients of 16.7%. This indicates the possibility that the difference can be used for narrowing the range of patients who possibly have Sjögren's syndrome. The percentage of the anti-HMG-1 antibody patients was statistically significantly higher among the patients of nine diseases other than polymyositis/dermatomyositis (PM/DM) than among the healthy persons. The percentage of the anti-HMG-2 antibody patients was statistically significantly higher among the patients of rheumatoid arthritis, systemic lupus erythematosus, Behçet's disease, primary biliary cirrhosis, and ulcerative colitis than among the healthy persons. The anti-HMG-2 antibody-positive patients were mostly anti-HMG-1 antibody-positive, but a small number of patients were anti-HMG-2 antibody-positive and anti-HMG-1 antibody-negative. Accordingly, measurement for both of the antibodies is preferably performed in order to perform diagnosis with a higher sensitivity.

The percentage of the patients who were both anti-HMG-1 antibody-positive and anti-HMG-2 antibody-positive was very high among the patients of primary biliary cirrhosis, rheumatoid arthritis, Sjögren's syndrome, and systemic lupus erythematosus. The percentage of such patients is considered to be equal to or higher than the percentage of anti-mitochondrion antibody-positive patients among the primary biliary cirrhosis patients out of the four diseases. Among the patients of the remaining three diseases, an antigen capable of reacting with sera of patients with such a high percentage has not been found. The percentage of the patients who were both anti-HMG-1 antibody-positive and anti-HMG-2 antibody-positive was also high among the scleroderma, ulcerative colitis, Crohn's disease, microscopic polyangiitis/polyarteritis nodosa and Behçet's disease. Among the patients of the above-mentioned three diseases, the HMG antigen is the first antigen which can react with sera with such a high percentage. Among the microscopic polyangiitis/polyarteritis nodosa patients, the anti-myeloperoxidase antibody-positive patients shows a high percentage, and the anti-HMG antibody-positive patients shows the next highest percentage. According to the present invention, it was found that the anti-HMG-1 antibody and the anti-HMG-2 antibody can both be detected among the patients of nine diseases other than polymyositis/dermatomyositis.

Measurement on antinuclear antibody was performed in parallel among the patients of these diseases by the indirect immunofluorescence assay, and the results were compared with the percentage of the HMG antigen-positive patients (see Table 5). The patients of seven out of ten diseases shows an equal or higher percentage than the percentage for the antinuclear antibody. These results demonstrate that measurement of HMG-1 and HMG-2 can be a method for diagnosing autoimmune diseases usable in lieu of detection of antinuclear antibody. Moreover, when combined with detection of antinuclear antibody, measurement of HMG-1 and HMG-2 can diagnose a wider range of autoimmune diseases more accurately.

Industrial Applicability

HMG-1 and HMG-2, which are common to rheumatoid arthritis, systemic lupus erythematosus, Sjögren's syndrome, Behçet's disease, scleroderma, primary biliary cirrhosis, microscopic polyangiitis/polyarteritis nodosa, ulcerative colitis, Crohn's disease, and autoimmune hepatitis, are specified. Accordingly, simple detection of antibodies using the antigens are now possible. Furthermore, a method and a measurement kit for measuring antibodies against both of the antigens using HMG-1 and HMG-2 are provided.

What is claimed is:

1. A kit for diagnosing an autoimmune disease, the kit comprising:
- a first antigen selected from the group consisting of a polypeptide having amino acid sequence indicated by SEQ ID NO:1, SEQ ID NO:4, SEQ ID NO:5, or a fragment of said polypeptide, wherein said polypeptide or fragment thereof specifically binds with an antibody from an autoimmune disease patient;
- a second antigen selected from the group consisting of a polypeptide having an amino acid sequence indicated by SEQ ID NO:2, SEQ ID NO:6, SEQ ID NO:8, or a fragment of said polypeptide, wherein said polypeptide or fragment thereof specifically binds with an antibody from an autoimmune disease patient;
- a first component for detecting a first antigen-antibody complex; and
- a second component for detecting a second antigen-antibody complex; wherein the autoimmune disease is selected from the group consisting of rheumatoid arthritis, human systemic lupus erythematosus. Sjögren's syndrome, Behçet's disease, primary biliary cirrhosis, microscopic polyangitis/polyarteritis nodosa, ulcerative colitis, Crohn's disease and autoimmune hepatitis.

2. A diagnostic drug for detecting an antibody of autoimmune diseases, wherein: the drug comprises, as an antigen:
- a polypeptide having an amino acid sequence indicated by SEQ ID NO:5, or a fragment of said polypeptide, wherein said polypeptide or fragment thereof specifically binds with an antibody from an autoimmune disease patient; or
- a polypeptide having an amino acid sequence indicated by SEQ ID NO:8, or a fragment of said polypeptide, wherein said polypeptide or fragment thereof specifically binds with an antibody from an autoimmune disease patient;
- wherein the autoimmune disease is selected from the group consisting of rheumatoid arthritis, human systemic lupus erythematosus, Sjögren's syndrome. Behçet's disease, primary biliary cirrhosis, microscopic polyangitis/polyarteritis nodosa, ulcerative colitis, Crohn's disease and autoimmune hepatitis.

3. The kit of claim 1, wherein the first antigen is SEQ ID NO:1.

4. The kit of claim 1, wherein the second antigen is SEQ ID NO:2.

5. The kit of claim 1, wherein the first antigen is SEQ ID NO:1, and the second antigen is SEQ ID NO:2.

* * * * *

SEQUENCE LISTING

<160> NUMBER OF SEQ ID NOS: 13

<210> SEQ ID NO 1
<211> LENGTH: 214
<212> TYPE: PRT
<213> ORGANISM: Homo sapiens

<400> SEQUENCE: 1

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Phe Lys Asp Pro Asn Ala Pro Lys Arg
                85                  90                  95

Pro Pro Ser Ala Phe Phe Leu Phe Cys Ser Glu Tyr Arg Pro Lys Ile
            100                 105                 110

Lys Gly Glu His Pro Gly Leu Ser Ile Gly Asp Val Ala Lys Lys Leu
        115                 120                 125

Gly Glu Met Trp Asn Asn Thr Ala Ala Asp Asp Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Glu Glu Glu Asp Glu Glu Asp
            180                 185                 190

Glu Glu Asp Glu Glu Glu Glu Asp Glu Glu Asp Glu Asp Glu Glu
        195                 200                 205

Glu Asp Asp Asp Asp Glu
    210

<210> SEQ ID NO 2
<211> LENGTH: 208
<212> TYPE: PRT
<213> ORGANISM: Homo sapiens

<400> SEQUENCE: 2

Gly Lys Gly Asp Pro Asn Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ser Ser Val Asn Phe Ala Glu Phe Ser Lys Lys Cys Ser Glu Arg Trp
        35                  40                  45

Lys Thr Met Ser Ala Lys Glu Lys Ser Lys Phe Glu Asp Met Ala Lys
    50                  55                  60

Ser Asp Lys Ala Arg Tyr Asp Arg Glu Met Lys Asn Tyr Val Pro Pro
65                  70                  75                  80

Lys Gly Asp Lys Lys Gly Lys Lys Lys Asp Pro Asn Ala Pro Lys Arg
                85                  90                  95

-continued

```
Pro Pro Ser Ala Phe Phe Leu Phe Cys Ser Glu His Arg Pro Lys Ile
                100                 105                 110

Lys Ser Glu His Pro Gly Leu Ser Ile Gly Asp Thr Ala Lys Lys Leu
            115                 120                 125

Gly Glu Met Trp Ser Glu Gln Ser Ala Lys Asp Lys Gln Pro Tyr Glu
        130                 135                 140

Gln Lys Ala Ala Lys Leu Lys Glu Lys Tyr Glu Lys Asp Ile Ala Ala
145                 150                 155                 160

Tyr Arg Ala Lys Gly Lys Ser Glu Ala Gly Lys Lys Gly Pro Gly Arg
                165                 170                 175

Pro Thr Gly Ser Lys Lys Lys Asn Glu Pro Glu Asp Glu Glu Glu Glu
            180                 185                 190

Glu Glu Glu Glu Asp Glu Asp Glu Glu Glu Asp Glu Asp Glu Glu
        195                 200                 205
```

<210> SEQ ID NO 3
<211> LENGTH: 214
<212> TYPE: PRT
<213> ORGANISM: Bos taurus

<400> SEQUENCE: 3

```
Gly Lys Gly Asp Pro Lys Lys Pro Arg Gly Lys Met Ser Ser Tyr Ala
  1               5                  10                  15

Phe Phe Val Gln Thr Cys Arg Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
         50                  55                  60

Ala Asp Lys Ala Arg Tyr Glu Arg Glu Met Lys Thr Tyr Ile Pro Pro
 65                  70                  75                  80

Lys Gly Glu Thr Lys Lys Lys Phe Lys Asp Pro Asn Ala Pro Lys Arg
                 85                  90                  95

Pro Pro Ser Ala Phe Phe Leu Phe Cys Ser Glu Tyr Arg Pro Lys Ile
                100                 105                 110

Lys Gly Glu His Pro Gly Leu Ser Ile Gly Asp Val Ala Lys Lys Leu
            115                 120                 125

Gly Glu Met Trp Asn Asn Thr Ala Ala Asp Asp Lys Gln Pro Tyr Glu
        130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Lys Glu Glu Glu Glu Asp Glu Glu Asp
            180                 185                 190

Glu Glu Asp Glu Glu Glu Glu Asp Glu Glu Asp Glu Glu Glu Glu
        195                 200                 205

Glu Asp Asp Asp Asp Glu
    210
```

<210> SEQ ID NO 4
<211> LENGTH: 214
<212> TYPE: PRT
<213> ORGANISM: Sus scrofa

<400> SEQUENCE: 4

```
Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys His Pro Asp
             20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr Lys Lys Phe Lys Asp Pro Asn Ala Pro Lys Arg
             85                  90                  95

Pro Pro Ser Ala Phe Phe Leu Phe Cys Ser Glu Tyr Arg Pro Lys Ile
             100                 105                 110

Lys Gly Glu His Pro Gly Leu Ser Ile Gly Asp Val Ala Lys Lys Leu
             115                 120                 125

Gly Glu Met Trp Asn Asn Thr Ala Ala Asp Asp Lys His Pro Tyr Glu
 130                 135                 140

Lys Lys Ala Ala Lys Leu Lys Glu Lys Tyr Glu Lys Asp Ile Ala Ala
 145                 150                 155                 160

Tyr Arg Ala Lys Gly Lys Pro Asp Ala Ala Lys Lys Gly Val Val Lys
             165                 170                 175

Ala Glu Lys Ser Lys Lys Lys Glu Glu Glu Asp Glu Glu Asp
             180                 185                 190

Glu Glu Asp Glu Glu Glu Glu Asp Glu Glu Asp Glu Glu Glu
             195                 200                 205

Glu Asp Asp Asp Asp Glu
             210
```

<210> SEQ ID NO 5
<211> LENGTH: 214
<212> TYPE: PRT
<213> ORGANISM: Rattus rattus

<400> SEQUENCE: 5

```
Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys His Pro Asp
             20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr Lys Lys Phe Lys Asp Pro Asn Ala Pro Lys Arg
             85                  90                  95

Pro Pro Ser Ala Phe Phe Leu Phe Cys Ser Glu Tyr Arg Pro Lys Ile
             100                 105                 110

Lys Gly Glu His Pro Gly Leu Ser Ile Gly Asp Val Ala Lys Lys Leu
             115                 120                 125

Gly Glu Met Trp Asn Asn Thr Ala Ala Asp Asp Lys His Pro Tyr Glu
 130                 135                 140

Lys Lys Ala Ala Lys Leu Lys Glu Lys Tyr Glu Lys Asp Ile Ala Ala
```

```
                    145                 150                 155                 160
Tyr Arg Ala Lys Gly Lys Pro Asp Ala Ala Lys Lys Gly Val Val Lys
                165                 170                 175
Ala Glu Lys Ser Lys Lys Lys Glu Glu Asp Glu Glu Asp
            180                 185                 190
Glu Glu Asp Glu Glu Glu Glu Glu Glu Asp Glu Glu Glu
        195                 200                 205
Glu Asp Asp Asp Glu
    210

<210> SEQ ID NO 6
<211> LENGTH: 209
<212> TYPE: PRT
<213> ORGANISM: Sus scrofa

<400> SEQUENCE: 6

Gly Lys Gly Asp Pro Asn Lys Pro Arg Gly Lys Met Ser Ser Tyr Ala
  1               5                  10                  15
Phe Phe Val Gln Thr Cys Arg Glu Glu His Lys Lys Lys His Pro Asp
                20                  25                  30
Ser Ser Val Asn Phe Ala Glu Phe Ser Lys Lys Cys Ser Glu Arg Trp
            35                  40                  45
Lys Thr Met Ser Ala Lys Glu Lys Ser Lys Phe Glu Asp Met Ala Lys
         50                  55                  60
Ser Asp Lys Ala Arg Tyr Asp Arg Glu Met Lys Asn Tyr Val Pro Pro
 65                  70                  75                  80
Lys Gly Asp Lys Lys Gly Lys Lys Asp Pro Asn Ala Pro Lys Arg
                85                  90                  95
Pro Pro Ser Ala Phe Phe Leu Phe Cys Ser Glu His Arg Pro Lys Ile
            100                 105                 110
Lys Ser Glu His Pro Gly Leu Ser Ile Gly Asp Thr Ala Lys Lys Leu
        115                 120                 125
Gly Glu Met Trp Ser Glu Gln Ser Ala Lys Asp Lys Gln Pro Tyr Glu
    130                 135                 140
Gln Lys Ala Ala Lys Leu Lys Glu Lys Tyr Glu Lys Asp Ile Ala Ala
145                 150                 155                 160
Tyr Arg Ala Lys Gly Lys Gly Glu Ala Gly Lys Lys Gly Pro Gly Arg
                165                 170                 175
Pro Thr Gly Ser Lys Lys Lys Asn Glu Pro Glu Asp Glu Glu Glu Glu
            180                 185                 190
Glu Glu Glu Glu Glu Asp Glu Asp Glu Glu Glu Asp Glu Asp Glu
        195                 200                 205
Glu

<210> SEQ ID NO 7
<211> LENGTH: 185
<212> TYPE: PRT
<213> ORGANISM: Bos taurus
<220> FEATURE:
<221> NAME/KEY: MOD_RES
<222> LOCATION: (39)
<223> OTHER INFORMATION: Xaa = Glu or Arg
<221> NAME/KEY: MOD_RES
<222> LOCATION: (149)
<223> OTHER INFORMATION: Xaa = Any Amino Acid

<400> SEQUENCE: 7

Gly Lys Gly Asp Pro Asn Lys Pro Arg Gly Lys Met Ser Ser Tyr Ala
```

```
                1               5              10              15

Phe Phe Val Gln Thr Ser Arg Glu Glu His Lys Lys His Pro Asp
                    20                  25                  30

Ala Ser Val Asn Phe Ser Xaa Trp Lys Thr Met Ser Ala Lys Glu Lys
                    35                  40                  45

Ser Lys Phe Glu Asp Met Ala Lys Ser Asp Lys Ala Arg Tyr Asp Arg
            50                  55                  60

Glu Met Lys Asn Tyr Val Pro Pro Lys Gly Asp Lys Lys Gly Lys Lys
    65                  70                  75                  80

Lys Asp Pro Asn Ala Pro Lys Arg Pro Pro Ser Ala Phe Phe Leu Phe
                        85                  90                  95

Ser Ala Glu His Arg Pro Lys Ile Lys Ala Glu His Pro Gly Leu Ser
                   100                 105                 110

Ile Gly Asp Thr Ala Lys Lys Leu Gly Glu Met Trp Ser Gln Gln Ser
                   115                 120                 125

Ala Lys Asp Lys Gln Pro Tyr Glu Glu Lys Ala Ser Lys Leu Lys Glu
                   130                 135                 140

Lys Tyr Glu Lys Xaa Ala Ala Tyr Arg Ala Lys Gly Lys Ser Glu Ala
    145                 150                 155                 160

Gly Lys Lys Gly Pro Gly Arg Pro Thr Gly Ser Lys Lys Lys Asn Glu
                       165                 170                 175

Pro Glu Asp Glu Glu Glu Glu Glu
                       180                 185

<210> SEQ ID NO 8
<211> LENGTH: 209
<212> TYPE: PRT
<213> ORGANISM: Rattus rattus

<400> SEQUENCE: 8

Gly Lys Gly Asp Pro Asn Lys Pro Arg Gly Lys Met Ser Ser Tyr Ala
    1               5                  10                  15

Phe Phe Val Gln Thr Cys Arg Glu Glu His Lys Lys Lys His Pro Asp
                    20                  25                  30

Ser Ser Val Asn Phe Ala Glu Phe Ser Lys Lys Cys Ser Glu Arg Trp
                    35                  40                  45

Lys Thr Met Ser Ala Lys Glu Lys Ser Lys Phe Glu Asp Met Ala Lys
                50                  55                  60

Ser Asp Lys Ala Arg Tyr Asp Arg Glu Met Lys Asn Tyr Val Pro Pro
    65                  70                  75                  80

Lys Gly Asp Lys Lys Gly Lys Lys Asp Pro Asn Ala Pro Lys Arg
                        85                  90                  95

Pro Pro Ser Ala Phe Phe Leu Phe Cys Ser Glu His Arg Pro Lys Ile
                   100                 105                 110

Lys Ser Glu His Pro Gly Leu Ser Ile Gly Asp Thr Ala Lys Lys Leu
                   115                 120                 125

Gly Glu Met Trp Ser Glu Gln Ser Ala Lys Asp Lys Gln Pro Tyr Glu
                   130                 135                 140

Gln Lys Ala Ala Lys Leu Lys Glu Lys Tyr Glu Lys Asp Ile Ala Ala
    145                 150                 155                 160

Tyr Arg Ala Lys Gly Lys Ser Glu Val Gly Lys Lys Gly Pro Gly Arg
                       165                 170                 175

Pro Thr Gly Ser Lys Lys Lys Asn Glu Pro Glu Asp Glu Glu Glu Glu
                       180                 185                 190
```

Glu Glu Glu Glu Asp Asp Glu Asp Glu Glu Glu Asp Glu Asp Glu
        195                 200                 205

Glu

<210> SEQ ID NO 9
<211> LENGTH: 206
<212> TYPE: PRT
<213> ORGANISM: Gallus gallus

<400> SEQUENCE: 9

Gly Lys Gly Asp Pro Asn Lys Pro Arg Gly Lys Met Ser Ser Tyr Ala
 1               5                  10                  15

Tyr Phe Val Gln Thr Cys Pro Arg Glu His Lys Lys Lys His Pro Asp
                20                  25                  30

Ser Ser Val Asn Phe Ala Glu Phe Ser Arg Lys Cys Ser Glu Arg Trp
        35                  40                  45

Lys Thr Met Ser Ser Lys Glu Lys Gly Lys Phe Glu Glu Met Ala Lys
    50                  55                  60

Gly Asp Lys Ala Arg Tyr Asp Arg Glu Met Lys Asn Tyr Val Pro Pro
65                  70                  75                  80

Lys Gly Glu Lys Lys Gly Lys Lys Asp Pro Asn Ala Pro Lys Arg
                85                  90                  95

Pro Pro Ser Ala Phe Phe Leu Phe Cys Ser Glu His Arg Pro Lys Ile
                100                 105                 110

Lys Asn Asp His Pro Gly Leu Ser Ile Gly Asp Thr Ala Lys Lys Leu
                115                 120                 125

Gly Glu Met Trp Ser Glu Gln Ser Ala Lys Asp Lys Gln Pro Tyr Glu
        130                 135                 140

Gln Lys Ala Ala Lys Leu Lys Glu Lys Tyr Glu Lys Asp Ile Ala Ala
145                 150                 155                 160

Tyr Arg Ala Lys Ser Lys Ser Asp Ala Gly Lys Lys Gly Pro Gly Arg
                165                 170                 175

Pro Ala Gly Ser Lys Lys Lys Ala Glu Pro Glu Glu Glu Glu Glu Glu
                180                 185                 190

Glu Glu Asp Glu Glu Glu Glu Glu Glu Asp Glu Glu
        195                 200                 205

<210> SEQ ID NO 10
<211> LENGTH: 201
<212> TYPE: PRT
<213> ORGANISM: Gallus gallus

<400> SEQUENCE: 10

Ala Lys Gly Asp Pro Lys Lys Pro Lys Gly Lys Met Ser Ala Tyr Ala
 1               5                  10                  15

Phe Phe Val Gln Thr Cys Arg Glu Glu His Lys Lys Lys Asn Pro Glu
                20                  25                  30

Val Pro Val Asn Phe Ala Glu Phe Ser Lys Lys Cys Ser Glu Arg Trp
        35                  40                  45

Lys Thr Met Ser Ser Lys Glu Lys Ala Lys Phe Asp Glu Met Ala Lys
    50                  55                  60

Ala Asp Lys Val Arg Tyr Asp Arg Glu Met Lys Asp Tyr Gly Pro Ala
65                  70                  75                  80

Lys Gly Gly Lys Lys Lys Lys Asp Pro Asn Ala Pro Lys Arg Pro Pro
                85                  90                  95

Ser Gly Phe Phe Leu Phe Cys Ser Glu Phe Arg Pro Lys Ile Lys Ser

-continued

```
                100                 105                 110
Thr Asn Pro Gly Ile Ser Ile Gly Asp Val Ala Lys Lys Leu Gly Glu
        115                 120                 125

Met Trp Asn Asn Leu Ser Asp Gly Glu Lys Gln Pro Tyr Asn Asn Lys
130                 135                 140

Ala Ala Lys Leu Lys Glu Lys Tyr Glu Lys Asp Val Ala Asp Tyr Lys
145                 150                 155                 160

Ser Lys Gly Lys Phe Asp Gly Ala Lys Gly Ala Ala Thr Lys Ala Ala
                165                 170                 175

Arg Lys Lys Val Glu Glu Glu Asp Glu Glu Glu Glu Asp Glu Glu
                180                 185                 190

Glu Glu Asp Glu Asp Asp Asp Glu
        195                 200
```

<210> SEQ ID NO 11
<211> LENGTH: 208
<212> TYPE: PRT
<213> ORGANISM: Mus musculus

<400> SEQUENCE: 11

```
Gly Lys Gly Asp Pro Ile Lys Pro Leu Gly Lys Met Ser Ser Tyr Ala
1               5                   10                  15

Phe Phe Val Gln Thr Cys Arg Glu Glu His Lys Lys Lys His Pro Asn
            20                  25                  30

Ser Ser Val Asn Phe Ala Glu Ile Ser Lys Lys Cys Ser Lys Arg Trp
        35                  40                  45

Lys Thr Met Ser Ala Lys Glu Asn Ser Lys Phe Glu Asp Leu Ala Lys
    50                  55                  60

Ser Asp Lys Ala Cys Tyr Tyr Arg Glu Met Lys Asn Tyr Val Ser Pro
65                  70                  75                  80

Lys Gly Asp Lys Lys Gly Lys Lys Asp Pro Asn Ala Pro Lys Arg
                85                  90                  95

Pro Pro Ser Ala Phe Cys Leu Phe Cys Ser Glu Asn Arg Pro Lys Ile
                100                 105                 110

Lys Ile Glu Tyr Pro Gly Leu Ser Ile Gly Asp Thr Ala Lys Lys Leu
        115                 120                 125

Gly Glu Met Trp Ser Glu Gln Ser Ala Lys Glu Lys Gln Pro Tyr Glu
    130                 135                 140

Gln Lys Ala Ala Lys Leu Lys Glu Lys Tyr Glu Lys Asp Phe Ala Ala
145                 150                 155                 160

Tyr Arg Val Lys Gly Lys Ser Glu Ala Gly Lys Lys Gly Pro Gly Arg
                165                 170                 175

Pro Ala Gly Ser Lys Lys Asn Asp Ser Glu Asp Glu Glu Glu Glu
                180                 185                 190

Glu Glu Glu Glu Glu Glu Asp Glu Glu Gly Glu Glu Glu Asp Glu Glu
        195                 200                 205
```

<210> SEQ ID NO 12
<211> LENGTH: 32
<212> TYPE: PRT
<213> ORGANISM: SYNTHETIC
<220> FEATURE:
<221> NAME/KEY: MOD_RES
<222> LOCATION: (22)
<223> OTHER INFORMATION: Xaa = Any Amino Acid

<400> SEQUENCE: 12

```
Gly Lys Gly Asp Pro Asn Lys Pro Arg Gly Lys Met Ser Ser Tyr Ala
 1               5                  10                  15

Phe Phe Val Gln Thr Xaa Arg Glu Glu His Lys Lys His Pro Asp
                 20              25              30

<210> SEQ ID NO 13
<211> LENGTH: 32
<212> TYPE: PRT
<213> ORGANISM: SYNTHETIC
<220> FEATURE:
<221> NAME/KEY: MOD_RES
<222> LOCATION: (22)
<223> OTHER INFORMATION: Xaa = Any Amino Acid

<400> SEQUENCE: 13

Gly Lys Gly Asp Pro Lys Lys Pro Arg Gly Lys Met Ser Ser Tyr Ala
 1               5                  10                  15

Phe Phe Val Gln Thr Xaa Arg Glu Glu His Lys Lys His Pro Asp
                 20              25              30
```